(12) United States Patent
Hillebrand et al.

(10) Patent No.: US 10,004,232 B2
(45) Date of Patent: *Jun. 26, 2018

(54) PIPERIDINE PYRAZOLES AS FUNGICIDES

(75) Inventors: Stefan Hillebrand, Neuss (DE);
Tomoki Tsuchiya, Lyons (FR);
Sebastian Hoffmann, Neuss (DE);
Pierre Cristau, Lyons (FR); Pierre Wasnaire, Düsseldorf (DE); Thomas Seitz, Langenfeld (DE); Juergen Benting, Leichlingen (DE); Ulrike Wachendorff-Neumann, Neuwied (DE); Peter Jan Schmidt, Saint-Genis Laval (FR)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 307 days.

This patent is subject to a terminal disclaimer.

(21) Appl. No.: 14/342,606

(22) PCT Filed: Sep. 11, 2012

(86) PCT No.: PCT/EP2012/067728
§ 371 (c)(1),
(2), (4) Date: Mar. 18, 2014

(87) PCT Pub. No.: WO2013/037768
PCT Pub. Date: Mar. 21, 2013

(65) Prior Publication Data
US 2014/0228404 A1  Aug. 14, 2014

(30) Foreign Application Priority Data
Sep. 15, 2011 (EP) ..................................... 11181383

(51) Int. Cl.
*C07D 417/14* (2006.01)
*A01N 43/80* (2006.01)

(52) U.S. Cl.
CPC ........... *A01N 43/80* (2013.01); *C07D 417/14* (2013.01)

(58) Field of Classification Search
None
See application file for complete search history.

(56) References Cited

U.S. PATENT DOCUMENTS

| | | | | |
|---|---|---|---|---|
| 8,524,743 | B2 * | 9/2013 | Cristau | C07D 417/14 514/210.18 |
| 9,144,238 | B2 * | 9/2015 | Hoffmann | A01N 25/00 |
| 2010/0056569 | A1 | 3/2010 | Nan et al. | |
| 2010/0137245 | A1 | 6/2010 | Cristau et al. | |
| 2010/0190828 | A1 | 7/2010 | Cristau et al. | |
| 2011/0046178 | A1 | 2/2011 | Cristau et al. | |
| 2011/0105429 | A1 | 5/2011 | Cristau et al. | |
| 2011/0124501 | A1 | 5/2011 | Cristau et al. | |
| 2011/0224257 | A1 | 9/2011 | Cristau et al. | |
| 2012/0122928 | A1 | 5/2012 | Tsuchiya et al. | |
| 2012/0122929 | A1 | 5/2012 | Tsuchiya et al. | |
| 2014/0005224 | A1 * | 1/2014 | Hillebrand | A01N 43/80 514/326 |

FOREIGN PATENT DOCUMENTS

| | | |
|---|---|---|
| JP | 60156601 A | 8/1985 |
| WO | WO-2005040159 A1 | 5/2005 |
| WO | WO-2006117521 A1 | 11/2006 |
| WO | WO-2007014290 A2 | 2/2007 |
| WO | WO-2007103187 A2 | 9/2007 |
| WO | WO-2007147336 A1 | 12/2007 |
| WO | WO-2008013622 A2 | 1/2008 |
| WO | WO-2008013925 A2 | 1/2008 |

(Continued)

OTHER PUBLICATIONS

Hartwig, John F., "Transition Metal Catalyzed Synthesis of Arylamines and Aryl Ethers from Aryl Halides and Triflates: Scope and Mechanism", Angew. Chem. Int. Ed., 1998, 37, pp. 2046-2067.
Collins, et al., "Organophosphorus Compounds. XVIII Synthesis of 2-Phenyl-2,3-dihydro-1H-1,2-benzazaphosphole 2-Sulfide by Pyrolysis of (2-Aminobenzyl)phenyldithiophosphinic Acid", Aust. J. Chem., 1983, 36, 2095-2110.
Qiao, et al., "Highly efficacious factor Xa inhibitors containing a-substituted phenylcycloalkyl P4 moieties", Bioorganic & Medicinal Chemistry Letters, 19, 2009, pp. 462-468.
Pashkevich, et al., "Fluoroalkyl containing mono- and bispyrazoles", English Translation, 1981, pp. 105-107.
Haberman, et al., "Dehydrative Sialylation with C2-Hemiketal Sialyl Donors", Organic Letters, 2003, vol. 5, No. 14, pp. 2539-2541.

(Continued)

Primary Examiner — Timothy R Rozof
(74) Attorney, Agent, or Firm — McBee Moore Woodward & Vanik IP, LLC

(57) ABSTRACT

The invention relates to heteroarylpiperidine and -piperazine derivatives of formula (I)

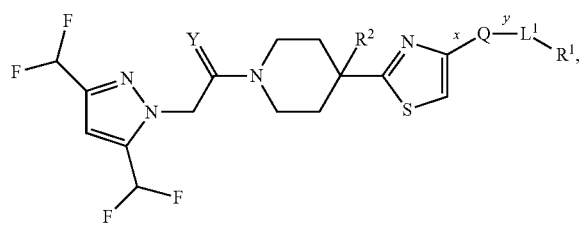

to agrochemically active salts thereof, to their use and also to methods and compositions for controlling phytopathogenic harmful fungi in and/or on plants or in and/or on seed of plants, to methods for producing such compositions and to treated seed, and also to the use thereof for controlling phytopathogenic harmful plants in agriculture, horticulture and forestry, in animal health, in materials protection and also in the household and hygiene sector. The present invention further relates to a method for producing heteroarylpiperidine and -piperazine derivatives.

14 Claims, No Drawings

(56) References Cited

FOREIGN PATENT DOCUMENTS

| WO | WO-2008091580 A2 | 7/2008 |
| WO | WO-2008091594 A2 | 7/2008 |
| WO | WO-2009055514 A2 | 4/2009 |
| WO | WO-2009094407 A2 | 7/2009 |
| WO | WO-2009094445 A2 | 7/2009 |
| WO | WO-2009132785 A1 | 11/2009 |
| WO | WO-2010037479 A1 | 4/2010 |
| WO | WO-2010065579 A2 | 6/2010 |
| WO | WO-2010066353 A1 | 6/2010 |
| WO | WO-2010123791 A1 | 10/2010 |
| WO | WO-2010149275 A1 | 12/2010 |
| WO | WO-2011051243 A1 | 5/2011 |
| WO | WO 2011/076699 A1 * | 6/2011 |
| WO | WO-2011076699 A1 | 6/2011 |
| WO | WO-2011085170 A1 | 7/2011 |
| WO | WO-2012020060 A1 | 2/2012 |
| WO | WO-2012025557 A1 | 3/2012 |
| WO | WO-2012055837 A1 | 5/2012 |
| WO | WO-2012082580 A2 | 6/2012 |

OTHER PUBLICATIONS

Dondoni, et al., "A New Convenient Preparation of 2-, 4, and 5-Thiazolecarboxaldehydes and Their Conversion into the Corresponding Carbonitrile N-Oxides: Synthesis of 3-Thiazolylisoxazoles and 3-Thiazolylisoxazolines", Synthesis, 1987, 11, pp. 998-1001.

Montalbetti, et al., "Amide bond formation and peptide coupling", Tetrahedron, 61, 2006, pp. 10827-10852.

International Search Report for PCT/EP2012/067728, dated Oct. 18, 2012, 12 pages.

* cited by examiner

PIPERIDINE PYRAZOLES AS FUNGICIDES

CROSS REFERENCE TO RELATED APPLICATIONS

This application is a § 371 National Stage Application of PCT/EP2012/067728, filed Sep. 11, 2012 which claims priority to EP 11181383.8, filed Sep. 15, 2011.

BACKGROUND

Field of the Invention

The invention relates to heteroarylpiperidine and -piperazine derivatives, to agrochemically active salts thereof, to their use and also to methods and compositions for controlling phytopathogenic harmful fungi in and/or on plants or in and/or on seed of plants, to methods for producing such compositions and to treated seed, and also to the use thereof for controlling phytopathogenic harmful plants in agriculture, horticulture and forestry, in animal health, in materials protection and also in the household and hygiene sector. The present invention further relates to a method for producing heteroarylpiperidine and -piperazine derivatives.

Description of the Related Art

It is already known that certain heterocyclically substituted thiazoles can be used as fungicidal crop protection agents (see WO 07/014,290, WO 08/013,925, WO 08/013,622, WO 08/091,594, WO 08/091,580, WO 09/055,514, WO 09/094,407, WO 09/094,445, WO 09/132,785, WO 10/037,479, WO 10/065,579, WO10/066,353, WO10/123,791, WO 10/149,275, WO 11/051,243, WO 11/085,170, WO 11/076,699, WO 12/020,060, WO 12/025,557, WO 12/082,580, WO 12/055,837). Particularly at relatively low application rates, however, the fungicidal activity of these compounds is not always sufficient.

SUMMARY

Given the continual increase in the environmental and economic requirements imposed on modern-day crop protection compositions, in respect, for example, of activity spectrum, toxicity, selectivity, application rate, formation of residues, and convenience of production, and since, moreover, problems may occur with resistance, for example, there is a continual object of developing new crop protection compositions, especially fungicides, which have advantages over their known counterparts at least in certain areas.

It has now been found that, surprisingly, the present heteroarylpiperidine and -piperazine derivatives achieve the stated objects at least in certain aspects, and are suitable for use as crop protection compositions, especially as fungicides.

The invention provides compounds of the formula (I),

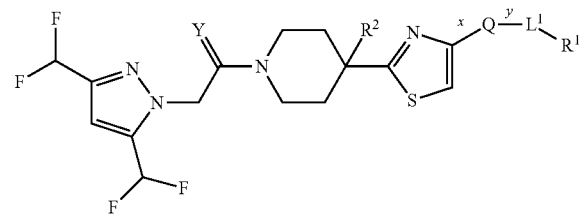

(I)

in which the definitions of radicals have the following meanings:
Y is oxygen or sulphur,
$R^2$ is hydrogen or halogen
Q is

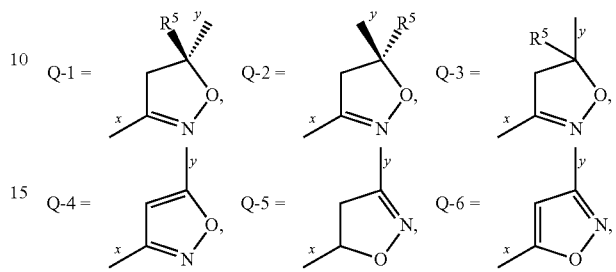

where the bond identified by "x" is bonded directly to the thiazole and the bond identified by "y" is bonded directly to $L^1$ or $R^1$,
$R^5$ is hydrogen, cyano, $C_1$-$C_3$ alkyl or $C_1$-$C_3$ haloalkyl,
$L^1$ is a direct bond, —$CH_2$—, —(C=O)—, sulphur or oxygen,
$R^1$ is phenyl which contains at least one substituent $Z^4$ and additionally two, three or four further substituents which independently are selected from $Z^4$ and $Z^1$,
or
$R^1$ is naphthyl, dihydronaphthalenyl, tetrahydronaphthalenyl, hexahydronaphthalenyl, octahydronaphthalenyl or indenyl which contains at least one substituent $Z^5$ and additionally contains two, three or four further substituents which independently are selected from $Z^5$ and $Z^1$,
or
$R^1$ is an optionally benzo-fused, substituted 5- or 6-membered heteroaryl which contains at least one substituent $Z^6$ and additionally contains two, three or four further substituents which on the carbon are selected independently of one another from $Z^6$ and $Z^1$ and on the nitrogen are selected independently of one another from $Z^6$ and $Z^2$,
or
$R^1$ is a $C_3$-$C_8$ cycloalkyl or is a $C_5$-$C_8$ cycloalkenyl which contains at least one substituent $Z^7$ and additionally contains two, three or four further substituents which independently of one another are selected from $Z^7$ and $Z^1$,
$Z^1$ is hydrogen, halogen, hydroxyl, nitro, cyano, alkyl, alkenyl, alkynyl, haloalkyl, haloalkenyl, haloalkynyl, cycloalkyl, halocycloalkyl, alkoxy, alkoxyalkyl, hydroxyalkyl, haloalkoxy, alkylcarbonyl, alkoxycarbonyl, alkylcycloalkyl, cycloalkoxyalkyl, cycloalkylamino, alkylthio, haloalkylthio, cycloalkylthio, cycloalkylalkyl, alkylcarbonyloxy, alkylcarbonylamino, haloalkylcarbonylamino, alkylcarbonylthio, alkylsulphinyl, haloalkylsulphinyl, alkylsulphonyloxy, haloalkylsulphonyloxy, alkylcycloalkylalkyl, —C(=O)$NR^3R^4$, —$NR^3R^4$, tri($C_1$-$C_2$ alkyl)silyl, or -$L^3Z^3$,
$Z^2$ is hydrogen, halogen, hydroxyl, nitro, cyano, alkyl, alkenyl, alkynyl, haloalkyl, haloalkenyl, haloalkynyl, cycloalkyl, halocycloalkyl, alkoxy, alkoxyalkyl, hydroxyalkyl, haloalkoxy, alkylcarbonyl, alkoxycarbonyl, alkylcycloalkyl, cycloalkoxyalkyl, cycloalkylamino, alkylthio, haloalkylthio, cycloalkylthio, cycloalkylalkyl, alkylcarbonyloxy, alkylcarbonylamino, haloalkylcarbonylamino, alkylcarbonylthio, alkylsulphinyl, haloalkylsulphinyl, alkylsulphonyloxy, haloalkylsulphonyloxy, alkylcycloalkylalkyl, —C(=O)NR$^3$R$^4$, —NR$^3$R$^4$ or tri(C$_1$-C$_2$ alkyl)silyl, Z$^3$ is a phenyl radical, naphthalenyl radical or a 5- or 6-membered heteroaryl radical which in each case may contain 0, 1, 2 or 3 substituents, the substituents being selected independently of one another from the following list:
  Substituents on the carbon: halogen, cyano, nitro, hydroxyl, amino, —SH, alkyl, alkenyl, alkynyl, haloalkyl, haloalkenyl, haloalkynyl, cycloalkyl, halocycloalkyl, alkoxyalkyl, alkylcarbonyl, haloalkylcarbonyl, alkoxycarbonyl, alkoxy, haloalkoxy, cycloalkoxy, halocycloalkoxy, alkenyloxy, alkynyloxy, alkoxyalkoxy, alkylamino, dialkylamino, alkylthio, haloalkylthio, alkylsulphinyl, haloalkylsulphinyl, alkylsulphonyl, haloalkylsulphonyl, trisilylalkyl or phenyl,
  Substituents on the nitrogen: hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, —C(=O)NR$^3$R$^4$, phenyl or benzyl, Z$^4$ is SH, C(=O)H, C$_7$-C$_8$ cycloalkyl, C$_7$-C$_8$ halocycloalkyl, cycloalkylcycloalkyl, halocycloalkylalkyl, cycloalkenyl, halocycloalkenyl, C$_5$-C$_6$ alkoxyalkyl, alkoxyalkoxyalkyl, alkylthioalkyl, alkylsulphinylalkyl, alkylsulphonylalkyl, alkylaminoalkyl, dialkylaminoalkyl, haloalkylaminoalkyl, cycloalkylaminoalkyl, C$_5$-C$_6$ alkylcarbonyl, haloalkylcarbonyl, cycloalkylcarbonyl, cycloalkoxycarbonyl, cycloalkylalkoxycarbonyl, cycloalkylaminocarbonyl, haloalkoxyalkyl, C$_5$-C$_6$ hydroxyalkyl, C$_5$-C$_6$ alkoxy, C$_5$-C$_6$ haloalkoxy, cycloalkoxy, halocycloalkoxy, cycloalkylalkoxy, alkenyloxy, haloalkenyloxy, alkynyloxy, haloalkynyloxy, alkoxyalkoxy, haloalkylcarbonyloxy, cycloalkylcarbonyloxy, alkylcarbonylalkoxy, C$_5$-C$_6$ alkylthio, C$_5$-C$_6$ haloalkylthio, C$_5$-C$_6$ alkylsulphinyl, C$_5$-C$_6$ haloalkylsulphinyl, alkylsulphonyl, haloalkylsulphonyl, cycloalkylsulphonyl, tri(C$_3$-C$_4$ alkyl)silyl, alkylsulphonylamino or haloalkylsulphonylamino, Z$^5$ is tri(C$_2$-C$_4$ alkyl)silyl, benzyl, phenyl, SH, C$_5$-C$_6$ alkoxy, C$_5$-C$_6$ haloalkoxy, C$_2$-C$_6$ alkenyloxy, C$_2$-C$_6$ alkynyloxy, C$_5$-C$_6$ alkylthio or C$_5$-C$_6$ haloalkylthio, Z$^6$ is
  Substituents on the carbon: SH, cycloalkylcycloalkyl or tri(C$_3$-C$_4$ alkyl)silyl,
  Substituents on the nitrogen: alkenyl, alkynyl, haloalkyl, haloalkenyl, haloalkynyl, cycloalkyl, halocycloalkyl, alkylcycloalkyl, cycloalkylalkyl, cycloalkylcycloalkyl, alkylsulphonyl, C(=O)H, benzyl or phenyl, Z$^7$ is cyano, halogen, hydroxyl, oxo, C$_1$-C$_4$ alkyl, C$_1$-C$_4$ haloalkyl, C$_1$-C$_4$ alkoxy, haloalkoxy, C$_1$-C$_4$ alkylthio, C$_1$-C$_4$ haloalkylthio or phenyl, L$^3$ is a direct bond, —CH$_2$—, —C(=O)—, sulphur, oxygen, —C(=O)O—, —C(=O)NH—, —OC(=O)— or —NHC(=O)—, R$^3$ and R$^4$, identically or differently and independently of one another, are hydrogen, alkyl, alkenyl, alkynyl, haloalkyl, cycloalkyl, benzyl or phenyl, and also salts, metal complexes and N-oxides of the compounds of the formula (I).

DETAILED DESCRIPTION OF A PREFERRED EMBODIMENT

Additionally provided is the use of the compounds of the formula (I) as fungicides. Heteroarylpiperidine and -piperazine derivatives of the formula (I) of the invention, and also their salts, metal complexes and N-oxides, are extremely suitable for the control of phytopathogenic harmful fungi. The aforementioned compounds of the invention exhibit in particular a strong fungicidal activity and can be used in crop protection, in the household and hygiene sector and in materials protection as well.

The compounds of the formula (I) may occur in pure form and also in the form of mixtures of different possible isomeric forms, more particularly of stereoisomers, such as E and Z, threo and erythro, and also optical isomers, such as R and S isomers or atrope isomers, and possibly in the form of tautomers as well. Claimed are the E and Z isomers, and also the threo and erythro isomers, and also the optical isomers, any desired mixtures of these isomers, and also the possible tautomeric forms.

The definitions of radicals for the compounds of the formula (I) according to the invention have the following definitions preferably, more preferably and very preferably:

Y preferably is oxygen or sulphur and more preferably is oxygen,

R$^2$ preferably is hydrogen or halogen, more preferably is hydrogen or fluorine and very preferably is hydrogen, Q preferably is Q-1, Q-2, Q-3, Q-4, Q-5 and Q-6, and more preferably is Q-3 and Q-4, wherein the bond identified by "x" is bonded directly to the thiazole and the bond identified by "y" is bonded directly to L$^1$ or R$^1$, R$^5$ preferably is hydrogen, cyano, methyl, ethyl, trifluoromethyl or difluoromethyl, or R$^5$ more preferably is hydrogen, cyano, methyl, trifluoromethyl or difluoromethyl, or R$^5$ very preferably is hydrogen, L$^1$ preferably is a direct bond or oxygen, L$^1$ more preferably is a direct bond, R$^1$ preferably is phenyl which contains at least one substituent Z$^4$ and additionally contains two or three further substituents which independently of one another are selected from Z$^4$ and Z$^1$, or R$^1$ more preferably is phenyl which contains at least one substituent Z$^4$ and additionally contains two further substituents which independently of one another are selected from Z$^4$ and Z$^1$, or R$^1$ preferably is naphthyl, dihydronaphthalenyl, tetrahydronaphthalenyl, hexahydronaphthalenyl, octahydronaphthalenyl or indenyl which contains at least one substituent Z$^5$ and additionally contains two or three further substituents which independently of one another are selected from Z$^5$ and Z$^1$, or R$^1$ more preferably is naphthyl, dihydronaphthalenyl, tetrahydronaphthalenyl or hexahydronaphthalenyl which contains at least one substituent Z$^5$ and additionally contains two further substituents which independently of one another are selected from Z$^5$ and Z$^1$, or R$^1$ preferably is an optionally benzo-fused, substituted 5- or 6-membered heteroaryl which contains at least one substituent Z$^6$ and additionally contains two or three further substituents which on the carbon are selected independently of one another from $Z^6$ and $Z^1$ and on the nitrogen are selected independently of one another from $Z^6$ and $Z^2$, or $R^1$ more preferably is furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl which contains at least one substituent $Z^6$ and additionally contains two further substituents which on the carbon are selected independently of one another from $Z^6$ and $Z^1$ and on the nitrogen are selected independently of one another from $Z^6$ and $Z^2$, or $R^1$ very preferably is furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl which may in each case contain 1 or 2 substituents, with one substituent being selected from $Z^6$ and optionally one further substituent being selected from the following list:

Substituents on the carbon: fluorine, chlorine, bromine, iodine, cyano, nitro, hydroxyl, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, 1-ethenyloxy, 2-propenyloxy, 2-propynyloxy, methylcarbonyloxy, trifluoroalkylcarbonyloxy, chloromethylcarbonyloxy, methylcarbonylamino, trifluoroalkylcarbonylamino, chloromethylcarbonylamino, methylthio, ethylthio, methylsulphinyl, methylsulphonyl, methylsulphonyloxy, trifluoroalkylsulphonyloxy, methylsulphonylamino or trifluoromethylsulphonylamino, Substituents on the nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, or $R^1$ more preferably is indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl which contains at least one substituent $Z^6$ and additionally contains two further substituents which on the carbon are selected independently of one another from $Z^6$ and $Z^1$ and on the nitrogen are selected independently of one another from $Z^6$ and $Z^2$, or $R^1$ more preferably is indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl which may in each case contain up to two substituents, the substituents being selected independently of one another from the following list:

Substituents on the carbon: fluorine, chlorine, bromine, iodine, methyl, methoxy, 2-propynyloxy, 2-propenyloxy, Substituents on the nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, $R^1$ preferably is a $C_3$-$C_8$ cycloalkyl or is a $C_5$-$C_8$ cycloalkenyl which contains at least one substituent $Z^7$ and additionally contains two or three further substituents which independently of one another are selected from $Z^7$ and $Z^1$, or $R^1$ more preferably is a $C_3$-$C_8$ cycloalkyl or is a $C_5$-$C_8$ cycloalkenyl which contains at least one substituent $Z^7$ and additionally contains two further substituents which independently of one another are selected from $Z^7$ and $Z^1$, or $Z^1$ preferably is hydrogen, halogen, cyano, hydroxyl, nitro, —C(=O)NR³R⁴, —NR³R⁴, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_8$ halocycloalkyl, $C_1$-$C_6$ alkoxy-$C_1$-$C_6$ alkyl, $C_1$-$C_6$ alkylcarbonyl, $C_1$-$C_6$ alkoxycarbonyl, alkoxy, haloalkoxy, $C_1$-$C_6$ alkylcarbonyloxy, $C_1$-$C_4$ alkylthio, $C_1$-$C_4$ haloalkylthio, $C_3$-$C_6$ cycloalkylthio, tri($C_1$-$C_2$ alkyl)silyl, or $-L^3Z^3$, $Z^1$ more preferably is hydrogen, chlorine, fluorine, bromine, cyano, nitro, —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)CH₃, —C(CH₃)₃, —CH=CH₂, —CH=CHCH₃, —CH₂CH=CH₂, —CH=CHCH₂CH₃, —CH₂CH=CHCH₃, —CH₂CH₂CH=CH₂, —C≡CH, —C≡CCH₃, —CH₂C≡CH, —C≡CCH₂CH₃, —CH$_2$C≡CCH$_3$, —CH$_2$CH$_2$C≡CH, —CF$_3$, —CFH$_2$, —CF$_2$CF$_3$, —CCl$_3$, cyclopropyl, cyclobutyl, cyclopentyl, cyclohexyl, —CH$_2$OCH$_3$, —CH$_2$OCH$_2$CH$_3$, —CH$_2$CH$_2$OCH$_3$, —CH$_2$OCH$_2$CH$_2$CH$_3$, —CH$_2$CH$_2$OCH$_2$CH$_3$, —CH$_2$CH$_2$CH$_2$OCH$_3$, —C(=O)CH$_3$, —C(=O)CH$_2$CH$_3$, C(=O)CH$_2$CH$_2$CH$_3$, C(=O)CH(CH$_3$)$_2$, —C(=O)CF$_3$, —C(=O)OCH$_3$, —C(=O)OCH$_2$CH$_3$, —C(=O)OCH$_2$CH$_2$CH$_3$, —C(=O)OCH(CH$_3$)$_2$, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, —OC(CH$_3$)$_3$, —OCF$_3$, —OCF$_2$H, —OCH$_2$CF$_3$, —OCF$_2$CF$_3$, O cyclohexyl, O cyclopentyl, O cyclopropyl, —SCH$_3$, —SCH$_2$CH$_3$, —SCH$_2$CH$_2$CH$_3$, —SCH(CH$_3$)$_2$, —SCH$_2$CH$_2$CH$_2$CH$_3$, —SCH$_2$CH(CH$_3$)$_2$, —SCH(CH$_3$)CH$_2$CH$_3$, —SC(CH$_3$)$_3$, —SCF$_3$, —SCF$_2$H, —SCH$_2$CF$_3$, —SCF$_2$CF$_3$, —S(=O)Me, —S(O)CF$_3$, —S(=O)$_2$Me, —S(O)$_2$CF$_3$, —OCH$_2$CH=CH$_2$, —OCH$_2$C≡CH, —OCH$_2$OCH$_3$, —OCH$_2$OCH$_2$CH$_3$, —OCH$_2$CH$_2$OCH$_3$, —OCH$_2$OCH(CH$_3$)$_2$, trimethylsilyl or phenyl which may contain 0, 1 or 2 substituents, the substituents being selected independently of one another from the following list:

chlorine, fluorine, bromine, cyano, nitro, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)CH$_3$, —C(CH$_3$)$_3$, —CH=CH$_2$, —CH$_2$CH=CH$_2$, —CH$_2$CH=CHCH$_3$, —CH$_2$CH$_2$CH=CH$_2$, —C≡CH, —C≡CCH$_3$, —CH$_2$C≡CH, —CF$_3$, —CF$_2$H, —CH$_2$OCH$_3$, —CH$_2$OCH$_2$CH$_3$, —CH$_2$CH$_2$OCH$_3$, —CH$_2$OCH$_2$CH$_2$CH$_3$, —CH$_2$CH$_2$OCH$_2$CH$_3$, —CH$_2$CH$_2$CH$_2$OCH$_3$, —C(=O)CH$_3$, —C(=O)CH$_2$CH$_3$, C(=O)CH$_2$CH$_2$CH$_3$, C(=O)CH(CH$_3$)$_2$, —C(=O)CF$_3$, —C(=O)OCH$_3$, —C(=O)OCH$_2$CH$_3$, —C(=O)OCH$_2$CH$_2$CH$_3$, —C(=O)OCH(CH$_3$)$_2$, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, —OC(CH$_3$)$_3$, —OCF$_3$, —OCF$_2$H, —OCH$_2$CF$_3$, —OCF$_2$CF$_3$, O—SCH$_3$, —SCH$_2$CH$_3$, —OCH$_2$C≡CH, —OCH$_2$OCH$_3$, $Z^2$ preferably is hydrogen, halogen, cyano, hydroxyl, nitro, —C(=O)NR$^3$R$^4$, —NR$^3$R$^4$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, C$_3$-C$_6$ cycloalkyl, C$_3$-C$_8$ halocycloalkyl, C$_1$-C$_6$ alkoxy-C$_1$-C$_6$ alkyl, C$_1$-C$_6$ alkoxycarbonyl, alkoxy, haloalkoxy, C$_1$-C$_6$ alkylcarbonyloxy, alkylthio, haloalkylthio, C$_3$-C$_6$ cycloalkylthio or tri(C$_1$-C$_2$ alkyl)silyl, $Z^2$ more preferably is hydrogen, chlorine, fluorine, bromine, cyano, nitro, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)CH$_3$, —C(CH$_3$)$_3$, —CH=CH$_2$, —CH=CHCH$_3$, —CH$_2$CH=CH$_2$, —CH=CHCH$_2$CH$_3$, —CH$_2$CH=CHCH$_3$, —CH$_2$CH$_2$CH=CH$_2$, —C≡CH, —C≡CCH$_3$, —CH$_2$C≡CH, —C≡CCH$_2$CH$_3$, —CH$_2$C≡CCH$_3$, —CH$_2$CH$_2$C≡CH, —CF$_3$, —CFH$_2$, —CF$_2$H, —CF$_2$CF$_3$, —CCl$_3$, cyclopropyl, cyclobutyl, cyclopentyl, cyclohexyl, —CH$_2$OCH$_3$, —CH$_2$OCH$_2$CH$_3$, —CH$_2$CH$_2$OCH$_3$, —CH$_2$OCH$_2$CH$_2$CH$_3$, —CH$_2$CH$_2$OCH$_2$CH$_3$, —CH$_2$CH$_2$CH$_2$OCH$_3$, —C(=O)CH$_3$, —C(=O)CH$_2$CH$_3$, C(=O)CH$_2$CH$_2$CH$_3$, C(=O)CH(CH$_3$)$_2$, —C(=O)CF$_3$, —C(=O)OCH$_3$, —C(=O)OCH$_2$CH$_3$, —C(=O)OCH$_2$CH$_2$CH$_3$, —C(=O)OCH(CH$_3$)$_2$, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, —OC(CH$_3$)$_3$, O cyclohexyl, O cyclopentyl, O cyclopropyl, —OCH$_2$CH=CH$_2$, —OCH$_2$C≡CH, —OCH$_2$OCH$_3$, —OCH$_2$OCH$_2$CH$_3$, —OCH$_2$CH$_2$OCH$_3$, —OCH$_2$OCH(CH$_3$)$_2$, trimethylsilyl, $Z^3$ preferably is a phenyl radical, naphthalenyl or a 5- or 6-membered heteroaryl radical which may contain up to two substituents, the substituents being selected independently of one another from the following list:
Substituents on the carbon: halogen, cyano, nitro, hydroxyl, amino, —SH, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_4$ alkoxyalkyl, C$_1$-C$_6$ alkylcarbonyl, C$_1$-C$_6$ haloalkylcarbonyl, C$_1$-C$_6$ alkoxycarbonyl, C$_1$-C$_4$ alkoxy, C$_1$-C$_4$ haloalkoxy, C$_2$-C$_6$ alkenyloxy, C$_2$-C$_6$ alkynyloxy, C$_1$-C$_4$ alkylthio, C$_1$-C$_4$ haloalkylthio, C$_1$-C$_4$ alkylsulphonyl, C$_1$-C$_4$ haloalkylsulphonyl or C$_1$-C$_4$ alkylamino, di(C$_1$-C$_4$ alkyl)amino,
Substituents on the nitrogen: C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, C$_1$-C$_4$ alkoxy-C$_1$-C$_4$ alkyl, phenyl, benzyl, C$_1$-C$_4$ haloalkylsulphonyl, C$_1$-C$_6$ alkoxycarbonyl, C$_1$-C$_6$ haloalkoxycarbonyl, phenylsulphonyl, C$_1$-C$_4$ alkylsulphonyl, —C(=O)H, or C$_1$-C$_3$ alkylcarbonyl, and $Z^3$ more preferably is a phenyl radical which may contain up to two substituents, the substituents being selected independently of one another from the following list:
chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methylamino, ethylamino, n-propylamino, 1-methylethylamino, 1,1-dimethylethylamino or dimethylamino, $Z^4$ preferably is C(=O)H, C$_7$-C$_8$ cycloalkyl, C$_3$-C$_6$ cycloalkyl-C$_3$-C$_6$-cycloalkyl, C$_3$-C$_6$ cycloalkenyl, C$_4$-C$_6$ alkoxy-C$_1$-C$_4$ alkyl, C$_3$-C$_6$ alkoxy-C$_2$-C$_4$ alkyl, C$_1$-C$_3$ alkoxy-C$_5$-C$_6$ alkoxy-C$_1$-C$_3$ alkyl, C$_1$-C$_4$ alkylthio-C$_1$-C$_2$ alkyl, C$_1$-C$_4$ alkylsulphinyl-C$_1$-C$_2$ alkyl, C$_1$-C$_4$ alkylsulphonyl-C$_1$-C$_2$ alkyl, C$_1$-C$_4$ alkylamino-C$_1$-C$_2$ alkyl, C$_1$-C$_2$-dialkylamino-C$_1$-C$_{12}$ alkyl, C$_1$-C$_4$ haloalkylamino-C$_1$-C$_2$ alkyl, C$_3$-C$_6$ cycloalkylamino-C$_1$-C$_2$ alkyl, C$_5$-C$_6$ alkylcarbonyl, C$_1$-C$_4$ haloalkylcarbonyl, C$_3$-C$_6$ cycloalkylcarbonyl, C$_3$-C$_6$ cycloalkoxycarbonyl, C$_3$-C$_6$ cycloalkyl-C$_1$-C$_2$ alkoxycarbonyl, C$_3$-C$_6$ cycloalkylaminocarbonyl, C$_1$-C$_4$ haloalkoxy-C$_1$-C$_2$ alkyl, C$_5$-C$_6$-hydroxyalkyl, C$_5$-C$_6$ alkoxy, C$_5$-C$_6$ haloalkoxy, C$_3$-C$_6$ cycloalkoxy, C$_3$-C$_6$ halocycloalkoxy, C$_3$-C$_6$ cycloalkylalkoxy, C$_2$-C$_6$ alkenyloxy, C$_2$-C$_6$ haloalkenyloxy, C$_2$-C$_6$ alkynyloxy, C$_2$-C$_6$ haloalkynyloxy, C$_1$-C$_4$ alkoxy-C$_1$-C$_4$ alkoxy, C$_1$-C$_4$ haloalkylcarbonyloxy, C$_3$-C$_6$ cycloalkylcarbonyloxy, C$_1$-C$_4$ alkylcarbonyl-C$_1$-C$_4$ alkoxy, C$_5$-C$_6$ alkylthio, C$_5$-C$_6$ haloalkylthio, C$_5$-C$_6$ alkylsulphinyl, C$_5$-C$_6$ haloalkylsulphinyl, C$_1$-C$_4$ alkylsulphonyl, haloalkylsulphonyl, C$_3$-C$_6$ cycloalkylsulphonyl, tri(C$_3$-C$_4$ alkyl)silyl, C$_1$-C$_4$ alkylsulphonylamino or C$_1$-C$_4$ haloalkylsulphonylamino, $Z^4$ more preferably is C(=O)H, cycloheptyl, 2-cyclopropylcyclopropyl, cyclohexenyl, n-butoxymethyl, n-propoxyethyl, methoxyethoxymethyl, ethoxyethoxymethyl, methylthiomethyl, ethylthiomethyl, methylsulphinylmethyl, ethylsulphinylmethyl, methyl sulphonylmethyl, ethyl sulphonylmethyl, methylaminomethyl, ethylaminomethyl, dimethylaminomethyl, trifluoromethylaminomethyl, cyclopropylaminomethyl, n-butylcarbonyl, n-pentylcarbonyl, trifluoromethylcarbonyl, cyclopropylcarbonyl, cyclohexylcarbonyl, cyclopropoxycarbonyl, cyclopentyloxycarbonyl, cyclohexyloxycarbonyl, cyclopoylaminocarbonyl, cyclopentylaminocarbonyl, cyclohexylaminocarbonyl, difluoromethoxymethyl, trifluoromethoxymethyl, n-pentoxy, halogen-n-pentoxy, cyclopropoxy, cyclopentyloxy, cyclohexyloxy, cyclopropylmethoxy, allyl, 3-methylbut-2-en-1-yloxy, prop-2-yn-1-yloxy, but-2-yn-1-yloxy, pent-2-yn-1-yloxy, haloalkynyloxy, methoxyethoxy, methoxypropoxy, ethoxyethoxy, trifluoropropanyloxy, trifluoromethylcarbonyloxy, cyclopropylcarbonyloxy, cyclopentylcarbonyloxy, cyclohexylcarbonyloxy, methylcarbonylmethoxy, pentylsulphonyl, methylsulphonyl, ethylsulphonyl, trifluoromethylsulphonyl, methylsulphonylamino, ethylsulphonylamino or trifluoromethylsulphonylamino, $Z^5$ preferably is benzyl, phenyl, $C_5$-$C_6$ alkoxy, $C_5$-$C_6$ haloalkoxy, $C_2$-$C_4$ alkenyloxy, $C_2$-$C_4$ alkynyloxy, $C_5$-$C_6$ alkylthio or $C_5$-$C_6$ haloalkylthio, $Z^6$ preferably is Substituents on the carbon: $C_3$-$C_6$ cycloalkylcyclopropyl, $C_3$-$C_6$ cycloalkylcyclohexyl or tri($C_3$-$C_4$ alkyl)silyl, Substituents on the nitrogen: $C_2$-$C_6$ alkenyl, $C_2$-$C_6$ alkynyl, $C_1$-$C_6$ haloalkyl, $C_3$-$C_6$ cycloalkyl, $C_1$-$C_4$ alkyl-$C_3$-$C_6$-cycloalkyl, $C_3$-$C_6$ cycloalkylcyclopropyl, $C_3$-$C_6$ cycloalkylcyclohexyl, $C_3$-$C_6$ cycloalkyl-$C_1$-$C_4$ alkyl, $C_1$-$C_4$ alkylsulphonyl, C(=O)H, benzyl or phenyl, $L^3$ preferably is a direct bond, —$CH_2$—, sulphur or oxygen, and more preferably is a direct bond, $R^3$ and $R^4$ preferably, identically or differently and independently of one another, are hydrogen, $C_1$-$C_4$ alkyl, $C_2$-$C_4$ alkenyl, $C_2$-$C_4$ alkynyl, $C_1$-$C_4$ haloalkyl, $C_5$-$C_6$ cycloalkyl, benzyl or phenyl, $R^3$ and $R^4$ more preferably, identically or differently and independently of one another, are hydrogen, methyl, ethyl, propyl, prop-2-yn-1-yl, 1,1,1-trifluoroethyl, cyclohexyl, benzyl or phenyl.

The general definition of the heteroarylpiperidine and -piperazine derivatives that can be used in accordance with the invention is provided by the formula (I). The definitions of radicals in the above radical definitions of the formula (I) and those specified below apply to the end products of the formula (I) and to all intermediates (see also below under "Explanations of the methods and intermediates") equally.

The radical definitions and explanations set out above and set out below, generally or in ranges of preference, may also be combined arbitrarily with one another, in other words between the respective ranges and preference ranges. They apply correspondingly for the end products and also for the precursors and intermediates. It is also possible for individual definitions to be omitted.

Preferred compounds of the formula (I) are those in which all of the radicals in each case have the preferred definitions specified above.

More preferred compounds of the formula (I) are those in which all of the radicals in each case have the more preferred definitions specified above.

Very preferred compounds of the formula (I) are those in which all of the radicals in each case have the very preferred definitions specified above.

Additionally preferred are compounds of the formula (I) and also agrochemically effective salts, metal complexes and N-oxides thereof in which:

Y is oxygen;
$R^2$ is hydrogen;
Q is Q-3;
$R^5$ is hydrogen;
$L^1$ is a direct bond;
$R^1$ is 4,5-dimethyl-2-(prop-2-yn-1-yloxy)phenyl or
$R^1$ is 2,6-difluoro-3-(prop-2-yn-1-yloxy)phenyl or
$R^1$ is 2,6-difluoro-4-(prop-2-yn-1-yloxy)phenyl or
$R^1$ is 2,6-difluoro-4-[(methylsulphonyl)amino]phenyl or
$R^1$ is 3-(allyloxy)-2,6-difluorophenyl.

The abovementioned definitions of radicals may be combined with one another in any desired way. It is also possible for individual definitions to be omitted.

According to the type of substituents defined above, the compounds of the formula (I) have acidic or basic properties and can form salts, possibly also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$— alkyl groups, mono-, di- and trialkanolamines of $C_1$-$C_4$— alkanols, choline and chlorocholine.

The salts obtainable in this way likewise have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main groups, especially aluminium, tin and lead, and also of the first to eighth transition groups, especially chromium, manganese, iron, cobalt, nickel, copper, zinc and others. Particular preference is given to the metal ions of the elements of the fourth period. The metals may be present in the different valencies that they can assume.

Optionally substituted groups may be mono- or polysubstituted, where the substituents in the case of poly substitutions may be the same or different.

In the definitions of the symbols given in the above formulae, collective terms were used, which are generally representative of the following substituents:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 8, preferably 1 to 6 and more preferably 1 to 3 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere like, for example, alkylthio, alkylsulphinyl, alkylsulphonyl, haloalkyl or haloalkylthio. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, formyl etc., are at the end.

Alkenyl: unsaturated, straight-chain or branched hydrocarbyl radicals having 2 to 8, preferably 2 to 6, carbon atoms and one double bond in any position, for example (but not limited to) $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. This definition also applies to alkenyl as part of a composite substituent, for example haloalkenyl etc., unless defined elsewhere.

Alkynyl: straight-chain or branched hydrocarbyl groups having 2 to 8, preferably 2 to 6, carbon atoms and one triple bond in any position, for example (but not limited to) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl. This definition also applies to alkynyl as part of a composite substituent, for example haloalkynyl etc., unless defined elsewhere.

Alkoxy: saturated, straight-chain or branched alkoxy radicals having 1 to 8, preferably 1 to 6 and more preferably 1 to 3 carbon atoms, for example (but not limited to) $C_1$-$C_6$-alkoxy such as methoxy, ethoxy, propoxy, 1-methylethoxy, butoxy, 1-methyl-propoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example haloalkoxy, alkynylalkoxy etc., unless defined elsewhere.

Alkylthio: saturated, straight-chain or branched alkylthio radicals having 1 to 8, preferably 1 to 6 and more preferably 1 to 3 carbon atoms, for example (but not limited to) $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio. This definition also applies to alkylthio as part of a composite substituent, for example haloalkylthio etc., unless defined elsewhere.

Alkoxycarbonyl: an alkoxy group which has 1 to 6, preferably 1 to 3, carbon atoms (as specified above) and is bonded to the skeleton via a carbonyl group (—CO—). This definition also applies to alkoxycarbonyl as part of a composite substituent, for example cycloalkylalkoxycarbonyl etc., unless defined elsewhere.

Alkylsulphinyl: saturated, straight-chain or branched alkylsulphinyl radicals having 1 to 8, preferably 1 to 6 and more preferably 1 to 3 carbon atoms, for example (but not limited to) $C_1$-$C_6$-alkylsulphinyl such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl. This definition also applies to alkylsulphinyl as part of a composite substituent, for example haloalkylsulphinyl etc., unless defined elsewhere.

Alkylsulphonyl: saturated, straight-chain or branched alkylsulphonyl radicals having 1 to 8, preferably 1 to 6 and more preferably 1 to 3 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl. This definition also applies to alkylsulphonyl as part of a composite substituent, for example alkylsulphonylalkyl etc., unless defined elsewhere.

Cycloalkyl: monocyclic, saturated hydrocarbyl groups having 3 to 10, preferably 3 to 8 and more preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Cycloalkenyl: monocyclic, partially unsaturated hydrocarbyl groups having 3 to 10, preferably 3 to 8 and more preferably 3 to 6 carbon ring members, for example (but not limited to) cyclopropenyl, cyclopentenyl and cyclohexenyl. This definition also applies to cycloalkenyl as part of a composite substituent, for example cycloalkenylalkyl etc., unless defined elsewhere.

Cycloalkoxy: monocyclic, saturated cycloalkyloxy radicals having 3 to 10, preferably 3 to 8 and more preferably 3 to 6 carbon ring members, for example (but not limited to) cyclopropyloxy, cyclopentyloxy and cyclohexyloxy. This definition also applies to cycloalkoxy as part of a composite substituent, for example cycloalkoxyalkyl etc., unless defined elsewhere.

Haloalkyl: straight-chain or branched alkyl groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere.

Haloalkylthio: straight-chain or branched alkylthio groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as part of a composite substituent, for example haloalkylthioalkyl etc., unless defined elsewhere.

Heteroaryl: 5 or 6-membered, fully unsaturated monocyclic ring system containing one to four heteroatoms from the group of oxygen, nitrogen and sulphur; if the ring contains more than one oxygen atom, they are not directly adjacent.

5-Membered heteroaryl containing one to four nitrogen atoms or one to three nitrogen atoms and one sulphur or oxygen atom: 5-membered heteroaryl ring groups which, in addition to carbon atoms, may contain one to four nitrogen atoms or one to three nitrogen atoms and one sulphur or oxygen atom as ring members, for example (but not limited to) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl.

Nitrogen-bonded 5-membered heteroaryl containing one to four nitrogen atoms, or benzofused nitrogen-bonded 5-membered heteroaryl containing one to three nitrogen atoms: 5-membered heteroaryl ring groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl.

6-Membered heteroaryl containing one to four nitrogen atoms: 6-membered heteroaryl ring groups which, in addition to carbon atoms, may contain one to three or one to four nitrogen atoms as ring members, for example (but not limited to) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl.

Benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl.

Benzofused 6-membered heteroaryl containing one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as part of a composite substituent, for example heteroarylalkyl etc., unless defined elsewhere.

Heterocyclyl: three- to fifteen-membered, preferably three- to nine-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl. This definition also applies to heterocyclyl as part of a composite substituent, for example heterocyclylalkyl etc., unless defined elsewhere.

Leaving group: $S_N1$ or $S_N2$ leaving group, for example chlorine, bromine, iodine, alkylsulphonates (—$OSO_2$-alkyl, e.g. —$OSO_2CH_3$, —$OSO_2CF_3$) or arylsulphonates (—$OSO_2$-aryl, e.g. —$OSO_2Ph$, —$OSO_2PhMe$).

Not included are those combinations which contravene the laws of nature and which the person skilled in the art would therefore rule out on the basis of his/her expert knowledge. Ring structures having three or more adjacent oxygen atoms, for example, are excluded.

Elucidation of the Preparation Processes and Intermediates

The piperidine pyrazoles of the formula (I) can be prepared in different ways. First of all, the possible processes are shown schematically below. Unless indicated otherwise, the radicals specified are each as defined above.

The processes according to the invention for preparing compounds of the formula (I) are optionally performed using one or more reaction auxiliaries.

Useful reaction auxiliaries are, if required, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, s- or t-butoxide or potassium methoxide, ethoxide, n- or i-propoxide, n-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN) or 1,8-diazabicyclo [5.4.0]-undec-7-ene (DBU).

The processes according to the invention are optionally performed using one or more diluents. Useful diluents include virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylene sulphone and hexamethylphosphoramide and DMPU.

The reaction temperatures in the process according to the invention can be varied within a relatively wide range. In general, the temperatures employed are between 0° C. and 250° C., preferably temperatures between 10° C. and 185° C.

The reaction time varies as a function of the scale of the reaction and of the reaction temperature, but is generally between a few minutes and 48 hours.

The processes according to the invention are generally carried out under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

Process A

Scheme 1: Process A

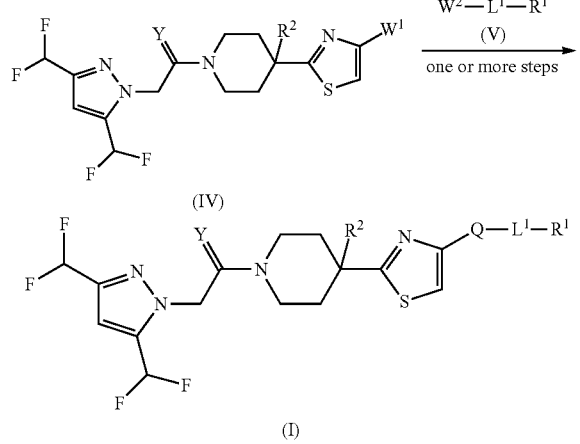

$W^1$ and $W^2$ are functional groups suitable for forming the desired isoxazoles or isoxazoline In general it is possible to prepare compounds of the formula (I) from corresponding compounds (IV) and (V) with suitable functional groups $W^1$ and $W^2$ (I) (see Scheme 1, Process A). The possible functional groups for $W^1$ and $W^2$ are capable under suitable reaction conditions of forming the desired isoxazole or isoxazoline ring Q (e.g. aldehydes, esters, carboxylic acids, amides, nitriles, alcohols, oximes, oxime chloride, halides, alkynes, alkenes, alkyl halides, methanesulphonates, trifluoromethanesulphonates, boronic acids and boronates). In the literature there are numerous methods for the preparation of isoxazoles or isoxazolines (see WO 2008/013622; *Comprehensive Heterocyclic Chemistry* Vol. 4-6, A. R. Katritzky and C. W. Rees editors, Pergamon Press, New York, 1984; *Comprehensive Heterocyclic Chemistry II*, Vol 2-4, A. R. Katritzky, C. W. Rees and E. F: Scriven editors, Pergamon Press, New York, 1996; *The Chemistry of Heterocyclic Compounds*, E. C. Taylor, editor, Wiley, New York; *Rodd's Chemistry of Carbon Compounds*, Vol. 2-4, Elsevier, New York; *Synthesis*, 1982, 6, 508-509; *Tetrahedron*, 2000, 56, 1057-1094; and literature cited therein).

Process B

Scheme 2: Process B

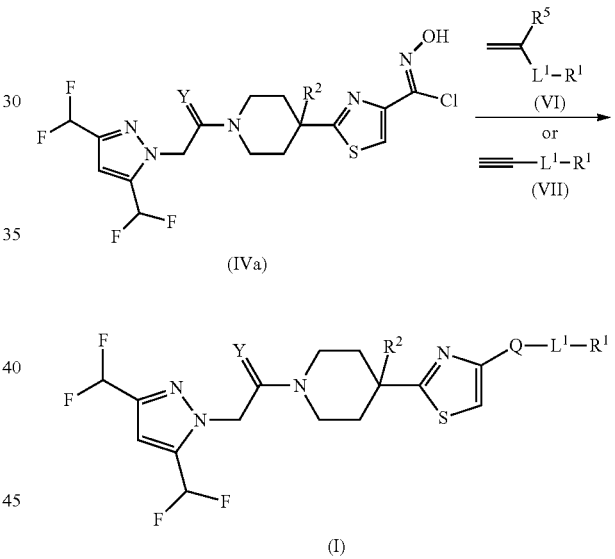

One particular possibility for preparing compounds of the formula (I) from corresponding compounds (IVa) by reaction with the compounds (VI) or (VII) is shown in Scheme 2.

A compound of the general formula (IVa) is obtained by condensing an aldehyde of the formula (XIX) with hydroxylamine and carrying out subsequent chlorination (see, for example, WO 05/0040159, WO 08/013,622 and *Synthesis*, 1987, 11, 998-1001). Aldehyde (XIX) and hydroxylamine are first of all brought to reaction (Scheme 3, step (a)). The corresponding oxime (XVIII) is subsequently chlorinated in the presence of a suitable chlorinating agent. Preferred chlorinating reagents are N-chlorosuccinimide, HClO, NaOCl, and chlorine. After step (a), the reaction mixture can be worked up by conventional methods or reacted further directly in step (b).

Scheme 3

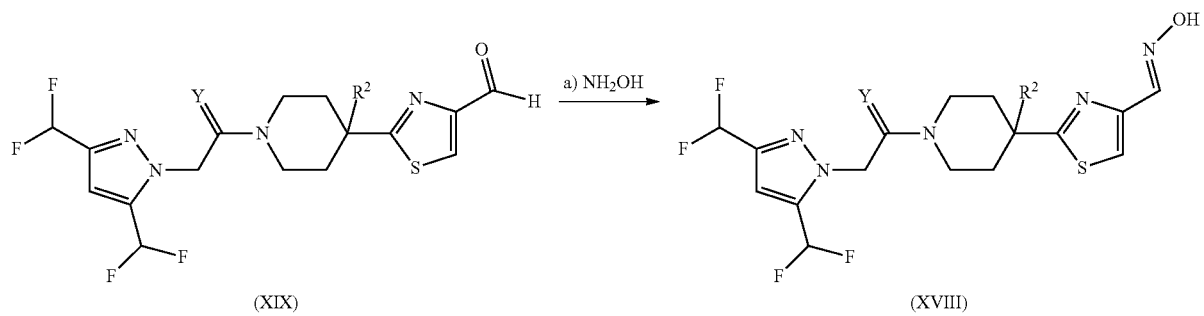

(XIX) → (XVIII)

b) chlorination

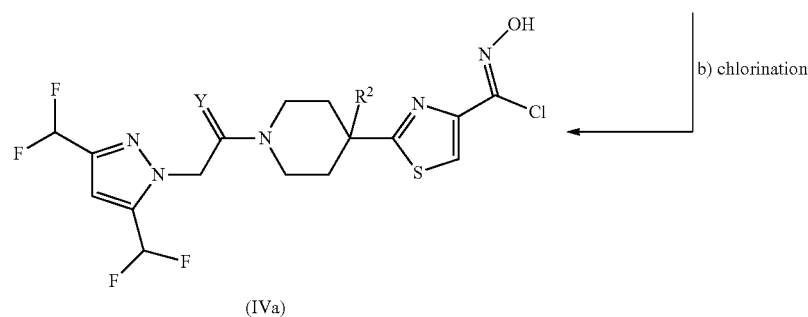

(IVa)

The alkenes (VI) and alkynes (VII) are available commercially or can be prepared from commercially available precursors by procedures described in the literature (e.g. from ketones or aldehydes by a Wittig or Horner-Wadsworth-Emmons olefination: *Chem. Rev.* 1989, 89, 863-927 and Julia olefination: *Tetrahedron Lett.*, 1973, 14, 4833-4836; Peterson olefination: *J. Org. Chem.* 1968, 33, 780; with Bestmann-Ohira's reagent: *Synthesis* 2004, 1, 59-62).

A compound of the general formula (I) is obtained from an alkene of the general formula (VI) or from an alkyne of the formula (VII) and compound (IVa) by a cycloaddition reaction (see, for example, WO 08/013,622 and *Synthesis*, 1987, 11, 998-1001).

Process B is carried out in the presence of a suitable base. Preferred bases are tertiary amines (e.g. triethylamine), alkali metal or alkaline earth metal carbonates (e.g. sodium carbonate or potassium carbonate), hydrogen carbonates and phosphates.

Process B is carried out preferably using one or more diluents. When carrying out Process B, the solvents contemplated are preferably inert organic solvents (such as ethyl acetate, tetrahydrofuran and DMF, for example). Another solvent contemplated is water. Process B may alternatively be carried out in an excess of the alkene (VI) or alkyne (VII).

Working up takes place by conventional methods. If necessary the compounds are purified by recrystallization or chromatography.

Process C

Scheme 4: Process C

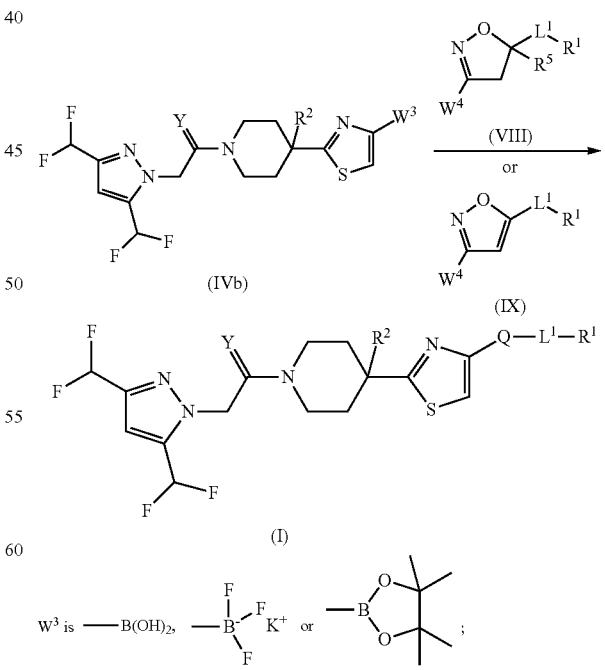

$W^3$ is —$B(OH)_2$, —$BF_3^- K^+$ or pinacol boronate;

$W^4$ is bromine or chlorine

One particular possibility for preparing compounds of the formula (I) from corresponding compounds (IVb) by reaction with the compounds (VIII) or (IX) by palladium-catalysed coupling reactions, such as, for example, the Suzuki reaction (*Angew. Chem. Int. Ed. Engl.*, 1998, 27, 2046; *A. Syn. Commun.*, 1981, 11, 7, 513), is shown in Scheme 4 (Process C).

The intermediate of the general formula (IVb) is obtained by borylation or by metal-halogen exchange with subsequent boron transmetallation from compounds of the formula (XXII) (see, for example, *Chemical Communications*, 2011, 460-462; *European Journal of Organic Chemistry*, 2007, 3212-3218; *Tetrahedron*, 2010, 8051-8059). The compounds of the formula (XXII) can be prepared from commercially available precursors by procedures described in the literature (see, for example, WO 2011/076699).

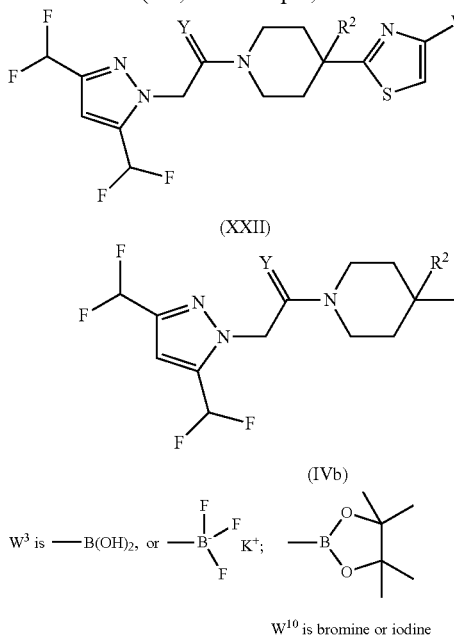

The isoxazoles or isoxazolines of the general formula (VIII) can be prepared from commercially available precursors (e.g. from hydroxycarbonimidoic dibromide or (hydroxyimino)acetic acid) by a cycloaddition reaction with an alkene (VI) or an alkyne (VII) (see *Organic Letters*, 2009, 1159-1162; *Liebigs Annalen der Chemie*, 1989, 985-90).

As solvents in Process C it is possible to use all customary solvents which are inert under the reaction conditions, and the reaction may be performed in mixtures of two or more of these solvents. The preferred solvents are N,N-dimethylformamide, dichloromethane, DMSO and tetrahydrofuran.

The reaction may be performed in the presence of the following additives: phosphines, such as 2-dicyclohexylphosphinobiphenyl, drying agents, e.g. 4 Å molecular sieve, and suitable bases, e.g. triethylamine, pyridine, sodium carbonate, sodium ethoxide or potassium phosphate.

Numerous commercially available copper(II) catalysts, palladium(0) catalysts or palladium(II) catalysts can be used in the reaction, but it is preferred in the reaction to use copper(II) acetate, tetrakistriphenylphosphinepalladium(0), [1,1-bis(diphenylphosphino)ferrocene]dichloropalladium (II), or palladium(II) acetate. The amount of catalyst used is at least 1% up to an excess, depending on the starting compound (IVb).

Working up takes place by conventional methods. If necessary the compounds are purified by recrystallization or chromatography.

Process D

Scheme 5: Process D

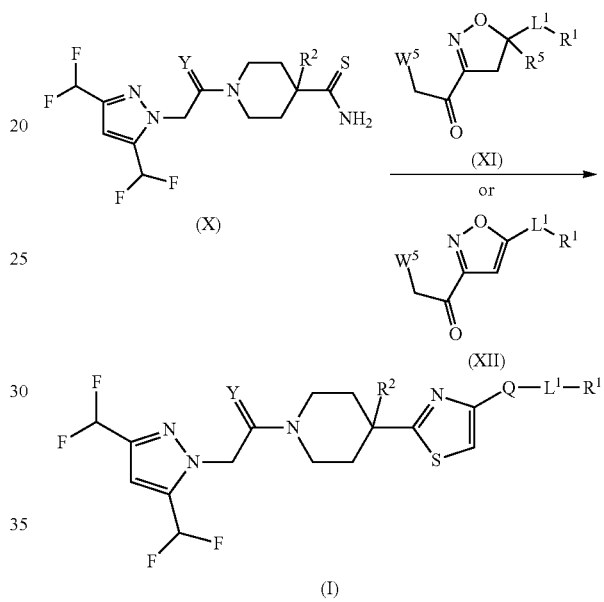

One particular possibility for the synthesis of compounds of the formula (I) from compounds (X) with the compounds (XI) or (XII) is shown in Scheme 5 (Process D).

Thiocarboxamides (X) are obtainable by methods known from the literature, as for example by thionation of the commercially available corresponding carboxamide through use of, for example, Lawesson's reagent (WO2008/013622, *Org. Synth.* Vol. 7, 1990, 372).

α-Haloketones or corresponding equivalents (e.g. p-toluenesulphonyloxy) are also obtainable by methods known from the literature (for example see WO2008/013622), (Scheme 6).

Scheme 6

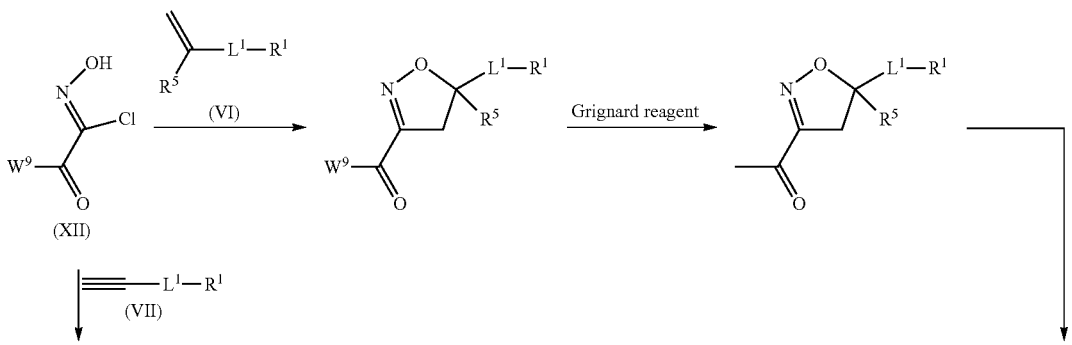

-continued

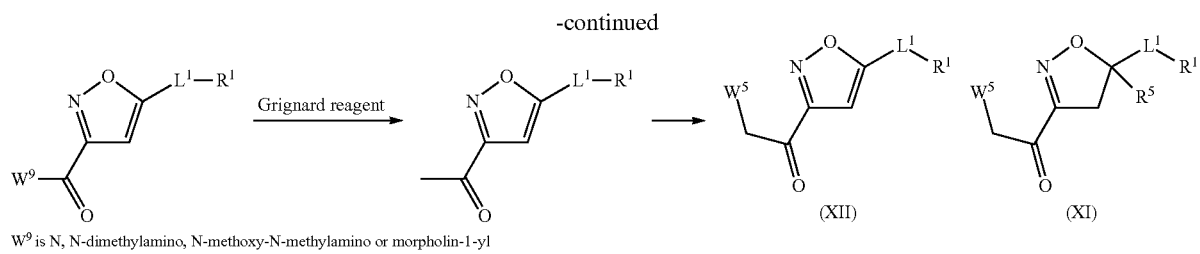

W⁹ is N, N-dimethylamino, N-methoxy-N-methylamino or morpholin-1-yl

The thiazoles (I) are obtained by a Hantzsch thiazole synthesis from the thiocarboxamides (X) and α-haloketones or corresponding equivalents (XI) or (XII) (see, for example, "Comprehensive heterocyclic Chemistry", Pergamon Press, 1984; Vol 6, pages 235-363, "Comprehensive heterocyclic Chemistry II", Pergamon Press, 1996; Vol 3, pages 373-474 and references cited therein, and WO 07/014,290).

Process D is preferably carried out using one or more diluents. When carrying out Process D, the solvents contemplated are preferably inert organic solvents (such as N,N-dimethylformamide and ethanol, for example).

The use of an auxiliary base, such as triethylamine, for example, is optional.

If necessary the compounds are purified by recrystallization or chromatography or may optionally also be used in the next step without purification beforehand.

Process E

Scheme 7: Process E

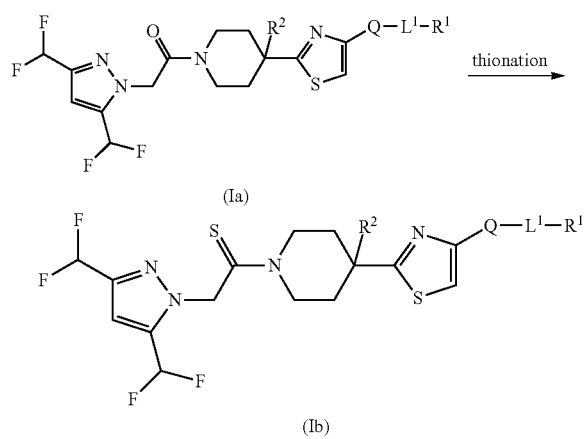

The amides (Ia) obtained when carrying out Process E according to the invention (Scheme 7) can be converted by means of methods described in the literature into the corresponding thioamides (Ib) (e.g. *Bioorganic & Medicinal Chemistry Letters*, 2009, 19(2), 462-468). In this case the compounds of the formula (Ia) are reacted typically with phosphorus pentasulphide or 2,4-bis(4-methoxyphenyl)-1,3-dithia-2,4-diphosphetane 2,4-disulphide (Lawesson's reagent).

Process E of the invention is carried out preferably using one or more diluents. The preferred solvents are toluene, tetrahydrofuran and 1,2-dimethoxyethane.

After the end of the reaction, the compounds (Ib) are separated from the reaction mixture by one of the conventional separation techniques. If necessary the compounds are purified by recrystallization or chromatography.

Process F

Scheme 8: Process F

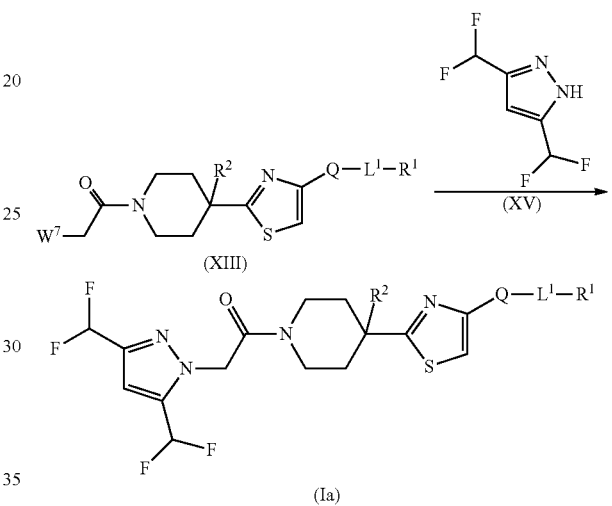

W⁷ is chlorine, bromine, iodine, p-toluenesulphonyloxy or methylsulphonyloxy

One possibility for preparing compounds of the formula (Ia) from corresponding compounds (XIII) with the compounds (XV) is shown in Scheme 8 (Process F).

The starting materials (XIII) in which W⁷ is a leaving group (e.g. chlorine, bromine, iodine, p-toluenesulphonyloxy or methylsulphonyloxy) can be prepared by means of methods described in the literature from compounds (XX), (XXI) or (III) (see Figure 1) (see, for example, mesylation: *Organic Letters*, 2003, 2539-2541; tosylation: JP60156601; halogenation: *Australian Journal of Chemistry*, 1983, 2095-2110). Typically, the compounds of the formula (XIIIa, W⁷=chlorine) are prepared starting from an amide of the formula (III) and chloroacetyl chloride. The compounds (XX) in (Figure 1) are prepared in analogy to Process F with glycolic acid or hydroxyacetyl chloride from (III) (see, for example, WO2007103187, WO2006117521, *Bioorganic & Medicinal Chemistry Letters*, 2007, 6326-6329).

FIG. 1

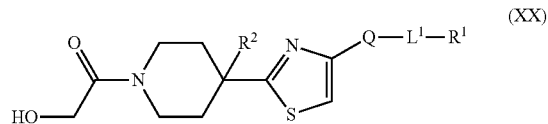

-continued

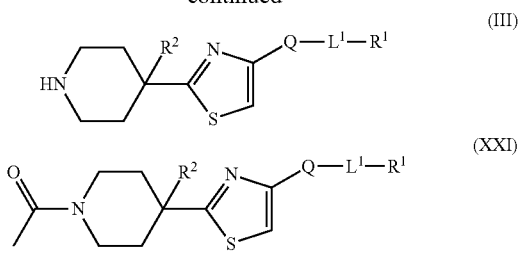

3,5-Bis(difluoromethyl)-1H-pyrazole (XV) is available commercially or can be prepared from commercially available precursors by processes described in the literature (*Zhurnal Vsesoyuznogo Khimicheskogo Obshchestva im. D. I. Mendeleeva*, 1981, 105-7).

In Process F at least one equivalent of a base (e.g. sodium hydride, potassium carbonate) is used in relation to the starting material of the general formula (XIII).

After the end of the reaction the compounds (Ia) are separated from the reaction mixture by one of the conventional separating techniques. If necessary the compounds are purified by recrystallization or chromatography.

Process G

Scheme 9: Process G

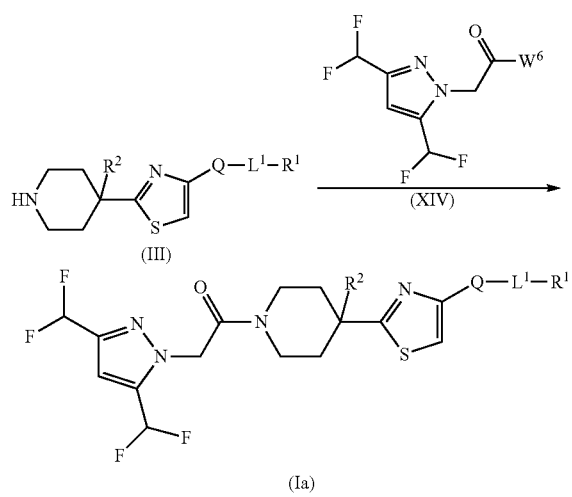

$W^6$ is fluorine, chlorine, bromine or iodine,

One possibility for preparing compounds of the formula (Ia) from corresponding compounds (III) with the compounds (XIV) is shown in Scheme 9 (Process G).

Compounds of the formula XXIV are known or can be prepared by processes described in the literature for the analogous compounds (see, for example, WO 2008/091580, WO 2007/014290 and WO 2008/091594).

A compound having the general formula (Ia) can be synthesized in analogy to the procedures described in the literature (see, for example, WO 2007/147336) by a coupling reaction of a compound with the corresponding general formula (III) with a substrate of the general formula (XIV), where $W^6$ is fluorine, chlorine, bromine or iodine, optionally in the presence of an acid scavenger/base.

At least one equivalent of an acid scavenger/base (e.g. Hünig base, triethylamine or commercially available polymeric acid scavengers) is used in relation to the starting material of the general formula (III). Where the starting material is a salt, at least two equivalents of the acid scavenger are needed.

Alternatively a compound of the formula (Ia) may also be synthesized from the corresponding compound of the formula (III) with a substrate of the formula (XIV) where $W^6$ is hydroxyl in the presence of a coupling reagent, in analogy to procedures described in the literature (e.g. Tetrahedron 2005, 61, 10827-10852, and references cited therein).

Suitable coupling reagents are, for example, peptide coupling reagents, for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.

After the end of the reaction the compounds (Ia) are separated from the reaction mixture by one of the conventional separation techniques. If necessary the compounds are purified by recrystallization or chromatography.

Process H

Scheme 10: Process H

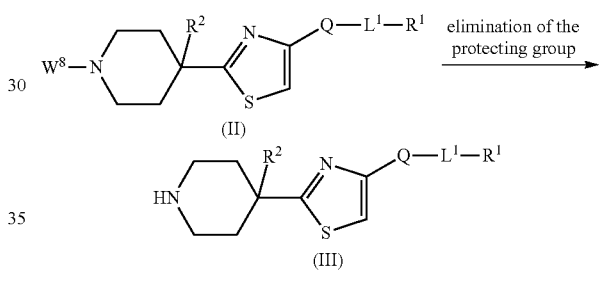

$W^8$ is acetyl, $C_1$-$C_4$ alkoxycarbonyl, benzyl or benzyloxycarbonyl

One possibility for preparing compounds of the formula (III) from corresponding compounds (II) is shown in Scheme 10 (Process H).

A compound of the formula (II) is converted into a compound of the formula (III) by suitable methods for the removal of protecting groups, which are described in the literature ("*Protective Groups in Organic Synthesis*"; Theodora W. Greene, Peter G. M. Wuts; Wiley-Interscience; third Edition; 1999; 494-653).

tert-Butoxycarbonyl and benzyloxycarbonyl protecting groups can be removed in the acidic medium (e.g. with hydrochloric acid or trifluoroacetic acid). Acetyl protecting groups can be removed under basic conditions (e.g. with potassium carbonate or caesium carbonate). Benzyl protecting groups can be removed hydrogenolytically with hydrogen in the presence of a catalyst (e.g. palladium on activated carbon).

After the end of the reaction the compounds (III) are separated from the reaction mixture by one of the conventional separating techniques. If necessary the compounds are purified by recrystallization or chromatography or may also, if desired, be used in the next step without purification beforehand. A further possibility is to isolate the compound of the general formula (III) in the form of a salt, e.g. the salt of hydrochloric acid or of trifluoroacetic acid.

Process I

Scheme 11: Process I

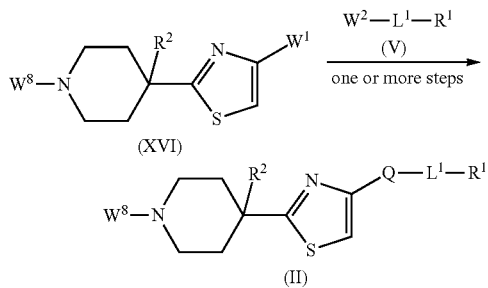

$W^1$ and $W^2$ are functional groups suitable for forming the desired isoxaole or isoxazoline
$W^8$ is acetyl, $C_1$-$C_4$ alkoxycarbonyl, benzyl or benzyloxycarbonyl One possibility for preparing the intermediate of the formula (II) from corresponding compounds (XVI) is shown in Scheme 11 (Process I). The possible functional groups for $W^1$ and $W^2$ are capable under suitable reaction conditions of forming the desired isoxazole or isoxazoline ring Q (e.g. aldehydes, esters, carboxylic acids, amides, nitriles, alcohols, oximes, oxime chloride, halides, alkynes, alkenes, alkyl halides, methanesulphonates, trifluoromethanesulphonates, boronic acids and boronates). Process I is carried out in analogy to Process A (Scheme 1).

Process J

Scheme 12: Process J

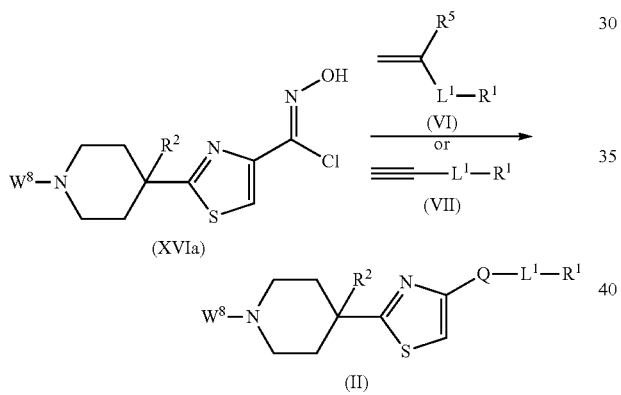

$W^8$ is acetyl, $C_1$-$C_4$ alkoxycarbonyl, benzyl or benzyloxycarbonyl

One particular possibility for preparing the intermediate of the formula (II) from corresponding compounds (XVIa) by reaction with the compounds (VI) or (VII) is shown in Scheme 12 (Process J). Process J is carried out in analogy to Process B (Scheme 2).

Process K

Scheme 13: Process K

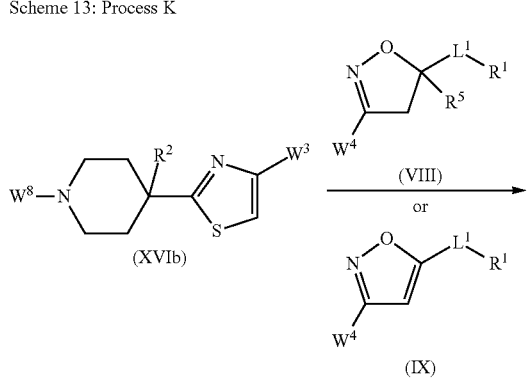

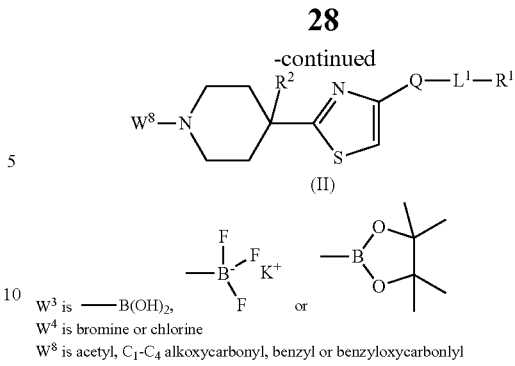

$W^3$ is —B(OH)$_2$, [BF$_3$K$^+$] or [Bpin]
$W^4$ is bromine or chlorine
$W^8$ is acetyl, $C_1$-$C_4$ alkoxycarbonyl, benzyl or benzyloxycarbonlyl Another particular possibility for preparing the intermediate of the formula (II) from corresponding compounds (XVIb) by reaction with the compounds (VIII) or (IX) is shown in Scheme 13 (Process K). Process K is carried out in analogy to Process C (Scheme 4).

Process L

Scheme 14: Process L

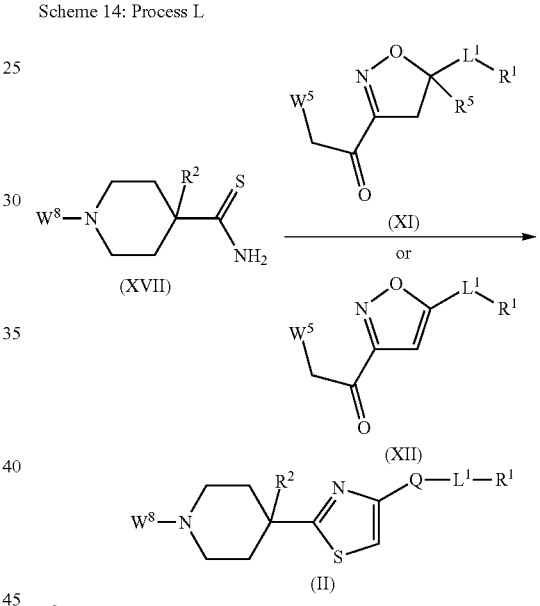

$W^5$ is iodine, bromine, chlorine, p-toluenesulphonyloxy or methylsulphonyloxy

One particular possibility for preparing the intermediate of the formula (II) from corresponding compounds (XVIa) by reaction with the compounds (XI) or (XII) is shown in Scheme 14 (Process L). Process L is carried out in analogy to Process D (Scheme 5).

It is recognized that certain reagents and reaction conditions, described above for preparing compounds of the formula (I), may not be compatible with certain functionalities present in the intermediate compounds. In these cases, the incorporation of protection/deprotection sequences or mutual conversions of functional groups into the synthesis is useful for obtaining the desired products. The use and selection of the protecting groups is obvious for the skilled person in chemical synthesis (see, for example, "*Protective Groups in Organic Synthesis*"; third edition; 494-653, and literature cited therein). The skilled person will recognize that in certain cases, following the introduction of a given reagent, as shown in an individual scheme, it may be necessary to carry out additional routine synthesis steps, which are not described in detail, in order to complete the synthesis of compounds of the formula (I). The skilled person will likewise recognize that it may be necessary to carry out a combination of steps, illustrated in the above schemes, in a different order from the sequence implied by that specifically shown, in order to prepare the compounds of the formula (I).

Likewise provided by the present invention are compounds of the formula (XIII)

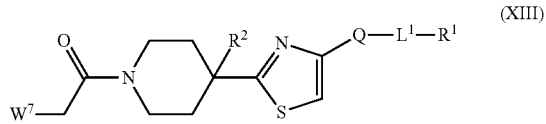
(XIII)

and also salts, metal complexes and N-oxides thereof, in which the symbols $W^7$, $R^2$, $Q$, $L^1$ and $R^1$ have the above-indicated general, preferred, more preferred or very preferred meanings.

Likewise provided by the present invention are compounds of the formula (II)

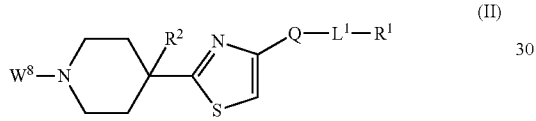
(II)

and also salts, metal complexes and N-oxides thereof, in which the symbols $W^8$, $R^2$, $Q$, $L^1$ and $R^1$ have the above-indicated general, preferred, more preferred or very preferred meanings.

New are compounds of the formula (III)

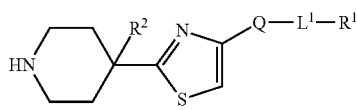
(III)

such as, for example, (IIIa), (IIIb), (IIIc) and (IIId),

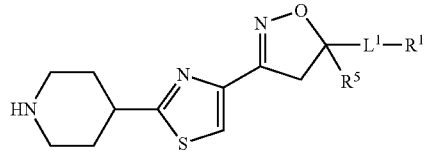
(IIIa)

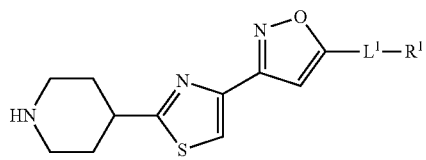
(IIIb)

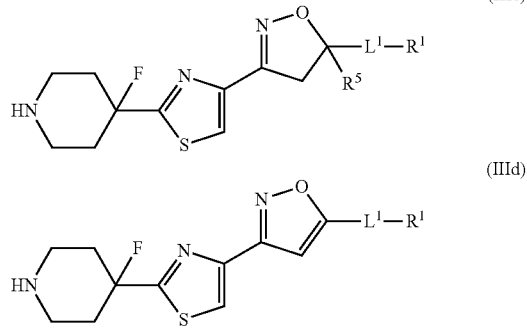
(IIIc)

(IIId)

and also salts, metal complexes and N-oxides thereof, in which the symbols $L^1$, $R^1$ and $R^5$ have the above-indicated general, preferred, more preferred or very preferred meanings.

New and likewise provided by the present invention is the compound of the formula (XIV-1)

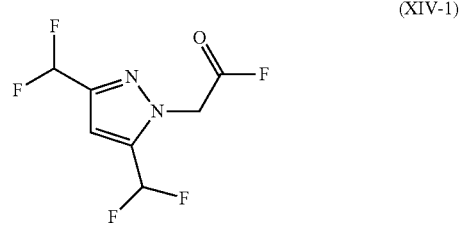 [SMILES: O=C(F)Cn1nc(C(F)F)cc1C(F)F]
(XIV-1)

and also salts, metal complexes and N-oxides thereof.

The present invention further relates to a composition for controlling unwanted microorganisms, comprising the inventive active ingredients. Said composition is preferably a fungicidal composition which comprises agriculturally suitable auxiliaries, solvents, carriers, surfactants or extenders.

The invention also relates to a method for controlling unwanted microorganisms, characterized in that the inventive active ingredients are applied to the phytopathogenic fungi and/or their habitat.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive compositions and formulations generally contain between 0.05 and 99% by weight, 0.01 and 98% by weight, preferably between 0.1 and 95% by weight, more preferably between 0.5 and 90% by weight of active ingredient, even more preferably between 10 and 70% by weight.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural and synthetic substances impregnated with active ingredient, and also microencapsulations in polymeric substances and in coating materials for seed, and also ULV cold-fogging and warm-fogging formulations.

The formulations mentioned can be prepared in a manner known per se, for example by mixing the active ingredients with at least one customary extender, solvent or diluent, emulsifier, dispersant, and/or binder or fixative, wetting agent, water repellent, if appropriate desiccants and UV stabilizers and, if appropriate, dyes and pigments, antifoams, preservatives, secondary thickeners, adhesives, giberellins and also further processing auxiliaries.

The inventive compositions include not only formulations which are already ready for use and can be applied with a suitable apparatus to the plant or the seed, but also commercial concentrates which have to be diluted with water prior to use.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry seed treatment, incrustation, coating with one or more coats, etc. It is also possible to deploy the active ingredients by the ultra-low volume method or to inject the active ingredient preparation or the active ingredient itself into the soil.

The invention further comprises a method for treating seed.

The invention further relates to seed which has been treated by one of the methods described in the previous paragraph. The inventive seeds are employed in methods for the protection of seed from unwanted microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after sowing or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European maize borer and/or the Western maize rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, giberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions.

Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The giberellins which may be present in the seed dressing formulations usable in accordance with the invention may preferably be giberellins A1, A3 (=gibberellic acid), A4 and A7; particular preference is given to using gibberellic acid. The giberellins are known (cf. R. Wegler "Chemie der Pflanzenschutz- and Schädlingsbekämpfungsmittel", vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying operation.

The inventive active ingredients or compositions have potent microbicidal activity and can be used for control of unwanted microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

The fact that the active ingredients are well tolerated by plants at the concentrations required for controlling plant diseases allows the treatment of above-ground parts of plants, of propagation stock and seeds, and of the soil.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, cotton, *Brassica* oil seeds such as *Brassica napus* (e.g. canola), *Brassica rapa*, *B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), *Ribesioidae* sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress, mustard, oilseed rape and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The term "parts" or "parts of plants" or "plant parts" has been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The inventive treatment method can be used for the treatment of genetically modified organisms (GMOs), for example plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which is/are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Depending on the plant species or plant cultivars, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect on plants. Accordingly, they are suitable for mobilizing the defence system of the plant against attack by unwanted phytopathogenic fungi and/or microorganisms and/or viruses. This may be one of the reasons for the enhanced activity of the inventive combinations, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi, the plants treated display a substantial degree of resistance to these unwanted phytopathogenic fungi. The inventive substances can therefore be used for protection of plants from attack by the pathogens mentioned within a certain period of time after the treatment. The period within which protection is achieved generally extends for from 1 to 10 days, preferably 1 to 7 days, after the treatment of the plants with the active ingredients.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated in accordance with the invention are resistant to one or more biotic stress factors, i.e. said plants have a better defence against animal and microbial pests, such as to nematodes, insects, mites, phytopathogenic fungi, bacteria, viruses and/or viroids.

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant cultivars which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, better health and resistance towards biotic and abiotic stress factors. Such plants are typically made by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. Plants can be made tolerant to glyphosate by various methods. For example, glyphosate-tolerant plants can be obtained by transforming the plant with a gene which encodes the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., 1988, J. Biol. Chem. 263, 4280-4289) or an *Eleusine* EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are, for example, plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (for example the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite the inhibition of the native HPPD enzyme by the HPPD inhibitor. Such plants are described in WO 99/34008 and WO 02/36787.

Tolerance of plants to HPPD inhibitors can also be improved by transforming plants with a gene encoding an enzyme prephenate dehydrogenase in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulphonylurea-tolerant plants and imidazolinone-tolerant plants has been described. Further sulphonylurea- and imidazolinone-tolerant plants have also been described.

Further plants tolerant to imidazolinone and/or sulphonylurea can be obtained by induced mutagenesis, by selection in cell cultures in the presence of the herbicide or by mutation breeding (cf., for example, for soya beans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al. (*Microbiology and Molecular Biology Reviews* 1998, 62, 807-813), updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or those proteins encoded by synthetic genes as described in U.S. patent application Ser. No. 12/249,016; or 2) a crystal protein from *Bacillus thuringiensis* or a portion thereof which is insecticidal in the presence of a second crystal protein other than *Bacillus thuringiensis* or a portion thereof, such as the binary toxin made up of the Cy34 and Cy35 crystal proteins (*Nat. Biotechnol.* 2001, 19, 668-72; *Applied Environm. Microbiol.* 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP08010791.5); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP) listed at http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102; or 9) a secreted protein from *Bacillus thuringiensis* or *Bacillus cereus* which is insecticidal in the presence of a crystal protein from *Bacillus thuringiensis*, such as the binary toxin made up of the proteins VIP3 and Cry1A or Cry1F (U.S. patent applications 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or 10) a protein according to point 9) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein).

Of course, insect-resistant transgenic plants, as used herein, also include any plant comprising a combination of genes encoding the proteins of any one of the abovementioned classes 1 to 10. In one embodiment, an insect-resistant plant contains more than one transgene encoding a protein of any one of the abovementioned classes 1 to 10, to expand the range of target insect species affected or to delay insect resistance development to the plants, by using different proteins insecticidal to the same target insect species but having a different mode of action, such as binding to different receptor binding sites in the insect.

In the present context, an "insect-resistant transgenic plant" additionally includes any plant containing at least one transgene comprising a sequence for production of double-stranded RNA which, after consumption of food by an insect pest, prevents the growth of this pest.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics, and include:

a) plants, such as cotton plants, which contain an altered form of cellulose synthase genes, b) plants, such as cotton plants, which contain an altered form of rsw2 or rsw3 homologous nucleic acids, such as cotton plants with an increased expression of sucrose phosphate synthase;

c) plants, such as cotton plants, with an increased expression of sucrose synthase;

d) plants, such as cotton plants, wherein the timing of the plasmodesmatal gating at the basis of the fibre cell is altered, for example through downregulation of fibre-selective β-1, 3-glucanase;

e) plants, such as cotton plants, which have fibres with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, which produce oil having a high oleic acid content;

b) plants, such as oilseed rape plants, which produce oil having a low linolenic acid content.

c) plants, such as oilseed rape plants, which produce oil having a low level of saturated fatty acids.

Plants or plant cultivars (obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which nonregulated status is being requested.

APHIS documents: Various documents which have been published by APHIS with regard to the petition or can be obtained from APHIS on request.

Particularly useful transgenic plants which may be treated according to the invention are plants which comprise one or more genes which encode one or more toxins, and are the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which should be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which should be mentioned include the varieties sold under the Clearfield® name (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gm-c.org/index.php?evidcode=&hstIDXCode=&gType=&AbbrCode=&atCode=&stCode=&coIDCode=&action=gm_crop_database&mode=Submit).

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, sizes, paper, wallpaper and cardboard, textiles, carpets, leather, wood, paints and plastic articles, cooling lubricants and other materials which can be infected with or destroyed by microorganisms. The range of materials to be protected also includes parts of production plants and buildings, for example cooling water circuits, cooling and heating systems, and ventilation and air conditioning systems, which may be impaired by the proliferation of microorganisms. Industrial materials within the scope of the present invention preferably include adhesives, sizes, paper and cardboard, leather, wood, paints, cooling lubricants and heat transfer fluids, more preferably wood. The inventive active ingredients or compositions may prevent adverse effects, such as rotting, decay, discoloration, decoloration or formation of mould. In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondita* or *Puccinia triticina*; *Uromyces* species, for example *Uromyces appendiculatus*;

diseases caused by pathogens from the group of the Oomycetes, for example *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*); *Colletotrichum* species, for example *Colletotrichum lindemuthianum*; *cycloconium* species, for example *cycloconium oleaginum*; *Diaporthe* species, for example *Diaporthe citri*; *Elsinoe* species, for example *Elsinoe faw-cettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola* and *M. fijiensis*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Tapesia* species, for example *Tapesia acuformis*; *Thielaviopsis* species, for example *Thielaviopsis basicola*;

ear and panicle diseases (including maize cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*;

*Verticilium* species, for example *Verticilium alboatrum*;

seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Taphrina* species, for example *Taphrina deformans*;

degenerative diseases of woody plants caused, for example, by *Esca* species, for example *Phaeomoniella chlamydospora* and *Phaeoacremonium aleophilum* and *Fomitiporia mediterranea*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllosticta leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the inventive active ingredients also have very good antimycotic activity. They have a very broad antimycotic activity spectrum, especially against dermatophytes and yeasts, moulds and diphasic fungi (for example against *Candida* species, such as *Candida albicans, Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means constitutes a restriction of the mycotic spectrum covered, and is merely of illustrative character.

The inventive active ingredients can therefore be used both in medical and in non-medical applications.

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions can thus be used to protect plants from attack by the pathogens mentioned for a certain period of time after treatment. The period for which protection is provided extends generally for 1 to 28 days, preferably for 1 to 14 days, more preferably for 1 to 10 days, even more preferably for 1 to 7 days, after the treatment of the plants with the active ingredients, or for up to 200 days after a seed treatment.

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

In some cases, the inventive compounds can, at particular concentrations or application rates, also be used as herbicides, safeners, growth regulators or compositions to improve plant properties, or as microbicides, for example as fungicides, antimycotics, bactericides, viricides (including compositions against viroids) or as compositions against MLO (Mycoplasma-like organisms) and RLO (Rickettsialike organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effects of the substances depend essentially on the time of application relative to the development stage of the plant and on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in orchards. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The plants listed can be treated in accordance with the invention in a particularly advantageous manner with the compounds of the general formula (I) and/or the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

EXAMPLES

General Note:
Unless indicated otherwise, all chromatographic purification and separation steps are carried out on silica gel and with a solvent gradient from 0:100 ethyl acetate/cyclohexane to 100:0 ethyl acetate/cyclohexane.

Preparation of Compound I-1

Step 1 tert-Butyl 4-{4-[5-(2-hydroxy-4,5-dimethylphenyl)-5-methyl-4,5-dihydro-1,2-oxazol-3-yl]-1,3-thiazol-2-yl}piperidine-1-carboxylate A solution of tert-butyl 4-{4-[(hydroxyimino)methyl]-1,3-thiazol-2-yl}piperidine-1-carboxylate (400 mg) in ethyl acetate (6 mL) was admixed with N-chlorosuccinimide (206 mg), 4,5-dimethyl-2-(prop-1-en-2-yl)phenol (1320 mg, purity: 50%), potassium hydrogencarbonate (643 mg) and subsequently one drop of water. The reaction mixture was stirred under reflux for 40 minutes. The reaction mixture was admixed at room temperature with ethyl acetate and water and was extracted with ethyl acetate. The organic extracts were dried over sodium sulphate and concentrated under reduced pressure. The residue was purified by chromatography. This gave tert-butyl 4-{4-[5-(2-hydroxy-4,5-dimethylphenyl)-5-methyl-4,5-dihydro-1,2-oxazol-3-yl]-1,3-thiazol-2-yl}piperidine-1-carboxylate (293 mg).

$^1$H NMR (DMSO-d$_6$): 9.34 (s, 1H), 7.94 (s, 1H), 7.12 (s, 1H), 6.63 (s, 1H), 4.05-3.95 (m, 2H), 3.52 (d, 1H), 3.48 (d, 1H), 3.25-3.15 (m, 1H), 2.88 (bs, 2H), 2.09 (s, 6H), 2.05-1.96 (m, 2H), 1.66 (s, 3H), 1.58-1.46 (m, 2H), 1.40 (s, 9H)

Step 2 tert-Butyl 4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidine-1-carboxylate (II-1)

A solution of tert-butyl 4-{4-[5-(2-hydroxy-4,5-dimethylphenyl)-5-methyl-4,5-dihydro-1,2-oxazol-3-yl]-1,3-thiazol-2-yl}piperidine-1-carboxylate (150 mg) and potassium carbonate (132 mg) in acetone (3 mL) was admixed at room temperature with 3-bromoprop-1-yne (42 mg, 80% strength in toluene). The reaction mixture was stirred at 60° C. for 6 hours. Thereafter the mixture was admixed with water and extracted with ethyl acetate. The combined organic phases were dried over sodium sulphate and concentrated. Purification by column chromatography gave tert-butyl 4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidine-1-carboxylate (64 mg).

$^1$H NMR (DMSO-d$_6$): 7.92 (s, 1H), 7.22 (s, 1H), 6.95 (s, 1H), 4.87 (s, 2H), 4.05-3.95 (m, 2H), 3.55 (d, 1H), 3.46 (d, 1H), 3.30 (s, 1H), 3.27-3.17 (m, 1H), 2.88 (bs, 2H), 2.19 (s, 3H), 2.15 (s, 3H), 2.04-1.96 (m, 2H), 1.66 (s, 3H), 1.58-1.46 (m, 2H), 1.40 (s, 9H)

Step 3

2-[3,5-Bis(difluoromethyl)-1H-pyrazol-1-yl]-1-[4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidin-1-yl]ethanone (I-1)

tert-Butyl 4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidine-1-carboxylate (64 mg) was admixed dropwise at room temperature with a 4-molar solution of hydrogen chloride (1.9 mL) in 1,4-dioxane. The solvent and excess hydrogen chloride were removed. This gave 4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidinium chloride.

A solution of [3,5-bis(difluoromethyl)-1H-pyrazol-1-yl] acetic acid (30 mg) in dichloromethane (20 mL) was admixed at 0° C. with oxalyl chloride (48 mg) and one drop of N,N-dimethylformamide. The reaction mixture was stirred at room temperature for 10 minutes. The solvent and the excess reagent were removed under reduced pressure. The residue was redissolved in dichloromethane and added dropwise at room temperature to a solution of 4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidinium chloride and triethylamine (38 mg) in dichloromethane (5 mL). The reaction mixture was stirred at room temperature. Thereafter it was admixed with concentrated sodium hydrogencarbonate solution, and the aqueous phase was separated off and extracted with ethyl acetate. The combined organic phases were dried over sodium sulphate and concentrated. Purification by column chromatography gave 2-[3,5-bis(difluoromethyl)-1H-pyrazol-1-yl]-1-[4-(4-{5-[4,5-dimethyl-2-(prop-2-yn-1-yloxy)phenyl]-5-methyl-4,5-dihydro-1,2-oxazol-3-yl}-1,3-thiazol-2-yl)piperidin-1-yl]ethanone (53 mg).

$^1$H NMR (DMSO-d$_6$): $\delta_{ppm}$: 7.94 (s, 1H), 7.23 (s, 1H), 7.18 (t, 1H), 7.03 (t, 1H), 6.96 (s, 1H), 6.91 (s, 1H), 5.43 (d, 1H), 5.35 (d, 1H), 4.87 (s, 2H), 4.38-4.30 (m, 1H), 4.00-3.92 (m, 1H), 3.72-3.63 (m, 1H), 3.60-3.44 (m, 2H), 3.40-3.20 (m, 2H), 2.86-2.78 (m, 1H), 2.19 (s, 3H), 2.15 (s, 3H), 2.13-2.00 (m, 2H), 1.82-1.70 (m, 1H), 1.67 (s, 3H), 1.60-1.58 (m, 1H)

Preparation of Compound I-2

Step 1 tert-Butyl 4-{4-[5-(2,6-difluoro-3-hydroxyphenyl)-4,5-dihydro-1,2-oxazol-3-yl]-1,3-thiazol-2-yl}piperidine-1-carboxylate A solution of tert-butyl 4-{4-[(hydroxyimino)methyl]-1,3-thiazol-2-yl}piperidine-1-carboxylate (1.278 g) in ethyl acetate (80 mL) was admixed with N-chlorosuccinimide (658 mg). The reaction mixture was stirred under reflux for 30 minutes. The reaction mixture was admixed at room temperature with 2,4-difluoro-3-vinylphenol (705 mg) and potassium hydrogencarbonate (822 mg) and then with one drop of water. After overnight stirring at room temperature, the reaction mixture was admixed with ethyl acetate and water and extracted with the ethyl acetate. The organic extracts were dried over sodium sulphate and concentrated under reduced pressure. The residue was purified by chromatography. This gave tert-butyl 4-{4-[5-(2,6-difluoro-3-hydroxyphenyl)-4,5-dihydro-1,2-oxazol-3-yl]-1,3-thiazol-2-yl}piperidine-1-carboxylate (680 mg).

$^1$H NMR (DMSO-d$_6$): 9.92 (s, 1H), 8.01 (s, 1H), 7.02-6.90 (m, 2H), 5.96 (dd, 1H), 4.02 (d, 2H), 3.88 (dd, 1H), 3.51 (dd, 1H), 2.90 (bs, 1H), 2.10-2.00 (m, 2H), 1.65-1.50 (m, 2H), 1.42 (s, 9H)

Step 2

2-[3,5-Bis(difluoromethyl)-1H-pyrazol-1-yl]-1-(4-{4-[5-(2,6-difluoro-3-hydroxyphenyl)-4,5-dihydro-1,2-oxazol-3-yl]-1,3-thiazol-2-yl}piperidin-1-yl)ethanone A solution of tert-butyl 4-{4-[5-(2,6-difluoro-3-hydroxyphenyl)-4,5-dihydro-1,2-oxazol-3-yl]-1,3-thiazol-2-yl}piperidine-1-carboxylate (374 mg) in dichloromethane was admixed dropwise at 0° C. with a 4-molar solution of hydrogen chloride (4.0 equivalents) in 1,4-dioxane. The reaction mixture was stirred at 0° C. and then slowly warmed to room temperature. After stirring for 5 hours, the solvent and excess hydrogen chloride were removed. This gave 4-{4-[5-(2,6-difluoro-3-hydroxyphenyl)-4,5-dihydro-1,2-oxazol-3-yl]-1,3-thiazol-2-yl}piperidinium chloride.

A solution of [3,5-bis(difluoromethyl)-1H-pyrazol-1-yl] acetic acid (160 mg) in dichloromethane (20 mL) was admixed at 0° C. with oxalyl chloride (275 mg) and one drop of N,N-dimethylformamide. The reaction mixture was stirred at room temperature for 2 hours. The solvent and the excess reagent were removed under reduced pressure. The solid residue was redissolved in dichloromethane and added dropwise at 0° C. to a solution of 4-{4-[5-(2,6-difluoro-3-hydroxyphenyl)-4,5-dihydro-1,2-oxazol-3-yl]-1,3-thiazol-2-yl}piperidinium chloride and triethylamine (10 equivalents) in dichloromethane (25 mL). The reaction mixture was stirred at room temperature overnight. Thereafter it was admixed with concentrated sodium hydrogencarbonate solution, and the aqueous phase was separated off and extracted with ethyl acetate. The combined organic phases were dried over sodium sulphate and concentrated. Purification by column chromatography gave 2-[3,5-bis(difluoromethyl)-1H-pyrazol-1-yl]-1-(4-{4-[5-(2,6-difluoro-3-hydroxyphenyl)-4,5-dihydro-1,2-oxazol-3-yl]-1,3-thiazol-2-yl}piperidin-1-yl)ethanone (177 mg).

$^1$H NMR (DMSO-$d_6$): 9.91 (s, 1H), 8.03 (s, 1H), 7.18 (t, 1H), 7.03 (t, 1H), 7.01-6.88 (m, 3H), 5.96 (dd, 1H), 5.38 (q, 2H), 4.35 (d, 1H), 4.02-3.83 (m, 2H), 3.51 (dd, 1H), 3.45-3.21 (m, 2H), 2.84 (t, 1H), 2.11 (t, 2H), 1.88-1.75 (m, 1H), 1.65-1.51 (m, 1H)

Step 3

2-[3,5-Bis(difluoromethyl)-1H-pyrazol-1-yl]-1-[4-(4-{5-[2,6-difluoro-3-(prop-2-yn-1-yloxy)phenyl]-4,5-dihydro-1,2-oxazol-3-yl}-1,3-thiazol-2-yl)piperidin-1-yl]ethanone (I-2)

A solution of 2-[3,5-bis(difluoromethyl)-1H-pyrazol-1-yl]-1-(4-{4-[5-(2,6-difluoro-3-hydroxyphenyl)-4,5-dihydro-1,2-oxazol-3-yl]-1,3-thiazol-2-yl}piperidin-1-yl)ethanone (85 mg) and potassium carbonate (31 mg) in N,N-dimethylformamide (10 mL) was admixed at room temperature with potassium iodide (13.5 mg) and 3-bromoprop-1-yne (35 mg 80% strength in toluene)). The reaction mixture was stirred at 80° C. for 4 hours. Thereafter the mixture was admixed with water and extracted with ethyl acetate. The combined organic phases were dried over sodium sulphate and concentrated. Purification by column chromatography gave 2-[3,5-bis(difluoromethyl)-1H-pyrazol-1-yl]-1-[4-(4-{5-[2,6-difluoro-3-(prop-2-yn-1-yloxy)phenyl]-4,5-dihydro-1,2-oxazol-3-yl}-1,3-thiazol-2-yl)piperidin-1-yl]ethanone (60 mg).

$^1$H NMR (DMSO-$d_6$): $\delta_{ppm}$: 8.03 (s, 1H), 7.38-7.26 (m, 1H), 7.18 (t, 1H), 7.20-7.10 (m, 1H), 7.03 (t, 1H), 6.91 (s, 1H), 5.99 (dd, 1H), 5.40 (q, 2H), 4.89 (d, 2H), 4.35 (d, 1H), 4.03-3.75 (m, 2H), 3.64 (t, 1H), 3.54 (dd, 1H), 3.47-3.20 (m, 2H), 2.84 (t, 1H), 2.12 (t, 2H), 1.88-1.74 (m, 1H), 1.65-1.50 (m, 1H)

Preparation of Compound I-4

1-[4-(4-{5-[3-(Allyloxy)-2,6-difluorophenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (I-4)

A solution of 2-[3,5-bis(difluoromethyl)-1H-pyrazol-1-yl]-1-(4-{4-[5-(2,6-difluoro-3-hydroxyphenyl)-4,5-dihydro-1,2-oxazol-3-yl]-1,3-thiazol-2-yl}piperidin-1-yl)ethanone (85 mg) and potassium carbonate (102 mg) in acetone (5 mL) was admixed at room temperature with allyl bromide (72 mg). The reaction mixture was stirred at reflux for 5 hours. Thereafter the mixture was admixed with water and extracted with ethyl acetate. The combined organic phases were dried over sodium sulphate and concentrated. Purification by column chromatography gave 1-[4-(4-{5-[3-(allyloxy)-2,6-difluorophenyl]-4,5-dihydro-1,2-oxazol-3-yl}-1,3-thiazol-2-yl)piperidin-1-yl]-2-[3,5-bis(difluoromethyl)-1H-pyrazol-1-yl]ethanone (55 mg).

$^1$H NMR (DMSO-$d_6$): 8.03 (s, 1H), 7.29-7.20 (m, 1H), 7.18 (t, 1H), 7.13-7.03 (m, 1H), 7.03 (t, 1H), 6.91 (s, 1H), 6.08-5.95 (m, 2H), 5.50-5.24 (m, 4H), 4.63 (dt, 2H), 4.35 (d, 1H), 4.05-3.85 (m, 2H), 3.53 (dd, 1H), 3.45-3.20 (m, 2H), 2.84 (t, 1H), 2.12 (t, 2H), 1.87-1.75 (m, 1H), 1.65-1.50 (m, 1H)

Preparation of Compound I-5

Step 1 tert-Butyl 4-{4-[5-(4-amino-2,6-difluorophenyl)-4,5-dihydro-1,2-oxazol-3-yl]-1,3-thiazol-2-yl}piperidine-1-carboxylate A solution of tert-butyl 4-{4-[(hydroxyimino)methyl]-1,3-thiazol-2-yl}piperidine-1-carboxylate (500 mg) in N,N-dimethylformamide (2 mL) was admixed with N-chlorosuccinimide (257 mg). The reaction mixture was stirred at 50° C. for 1 hour. The reaction mixture was admixed at room temperature with 3,5-difluoro-4-vinylaniline (324 mg) and triethylamine (0.67 mL). After stirring at 50° C. for 2 hours, the reaction mixture was admixed with ethyl acetate and water and extracted with ethyl acetate. The organic extracts were dried over sodium sulphate and concentrated under reduced pressure. The residue was purified by chromatography. This gave tert-butyl 4-{4-[5-(4-amino-2,6-difluorophenyl)-4,5-dihydro-1,2-oxazol-3-yl]-1,3-thiazol-2-yl}piperidine-1-carboxylate (400 mg).

$^1$H NMR (DMSO-$d_6$): 7.95 (s, 1H), 6.21 (d, 2H), 5.89 (s, 2H), 5.79 (dd, 1H), 4.05-3.97 (m, 2H), 3.73 (dd, 1H), 3.39 (dd, 1H), 3.30-3.20 (m, 1H), 2.89 (bs, 2H), 2.08-2.00 (m, 2H), 1.62-1.49 (m, 2H), 1.41 (s, 9H)

Step 2 tert-Butyl 4-[4-(5-{2,6-difluoro-4-[(methylsulphonyl)amino]phenyl}-4,5-dihydro-1,2-oxazol-3-yl)-1,3-thiazol-2-yl]piperidine-1-carboxylate (II-2)

A solution of tert-butyl 4-{4-[5-(4-amino-2,6-difluorophenyl)-4,5-dihydro-1,2-oxazol-3-yl]-1,3-thiazol-2-yl}piperidine-1-carboxylate (400 mg) in dichloromethane (10 mL) was admixed with methanesulphonyl chloride (109 mg) and pyridine (82 mg). The reaction mixture was stirred at room temperature overnight. The reaction mixture was again admixed at room temperature with pyridine (82 mg) and methanesulphonyl chloride (109 mg). After stirring at room temperature for 2 hours, the reaction mixture was admixed with 1N HCl solution and extracted with dichloromethane. The organic extracts were dried over sodium sulphate and concentrated under reduced pressure. The residue was purified by chromatography. This gave tert-butyl 4-[4-(5-{2,6-difluoro-4-[(methylsulphonyl)amino]phenyl}-4,5-dihydro-1,2-oxazol-3-yl)-1,3-thiazol-2-yl]piperidine-1-carboxylate (380 mg).

$^1$H NMR (DMSO-$d_6$): 7.99 (s, 1H), 6.89 (d, 2H), 5.93 (dd, 1H), 4.05-3.97 (m, 2H), 3.75 (dd, 1H), 3.49 (dd, 1H), 3.30-3.20 (m, 1H), 3.14 (s, 3H), 2.89 (bs, 2H), 2.08-2.00 (m, 2H), 1.62-1.50 (m, 2H), 1.41 (s, 9H)

Step 3

4-[4-(5-{2,6-Difluoro-4-[(methylsulphonyl)amino]phenyl}-4,5-dihydro-1,2-oxazol-3-yl)-1,3-thiazol-2-yl]piperidinium chloride (III-1)

tert-Butyl 4-[4-(5-{2,6-difluoro-4-[(methylsulphonyl)amino]phenyl}-4,5-dihydro-1,2-oxazol-3-yl)-1,3-thiazol-2-yl]piperidine-1-carboxylate (380 mg) was admixed dropwise at room temperature with a 4-molar solution of hydrogen chloride (2.6 mL) in 1,4-dioxane. The solvent and excess hydrogen chloride were removed. This gave 4-[4-(5-{2,6-difluoro-4-[(methylsulphonyl)amino]phenyl}-4,5-dihydro-1,2-oxazol-3-yl)-1,3-thiazol-2-yl]piperidinium chloride (380 mg).

$^1$H NMR (DMSO-$d_6$): 9.19 (bs, 1H), 8.94 (bs, 1H), 8.04 (s, 1H), 6.92 (d, 2H), 5.94 (dd, 1H), 3.90-3.70 (m, 2H), 3.55-3.30 (m, 4H), 3.13 (s, 3H), 3.08-2.97 (m, 2H), 2.25-2.17 (m, 2H), 2.02-1.90 (m, 2H)

Step 4

N-(4-{3-[2-(1-{[3,5-Bis(difluoromethyl)-1H-pyrazol-1-yl]acetyl}piperidin-4-yl)-1,3-thiazol-4-yl]-4,5-dihydro-1,2-oxazol-5-yl}-3,5-difluorophenyl)methanesulphonamide (I-5)

[3,5-Bis(difluoromethyl)-1H-pyrazol-1-yl]acetic acid (180 mg) and triethylamine (242 mg) were dissolved in dichloromethane (10 mL) and stirred for 10 minutes. 4-[4-(5-{2,6-Difluoro-4-[(methylsulphonyl)amino]phenyl}-4,5-dihydro-1,2-oxazol-3-yl)-1,3-thiazol-2-yl]piperidinium chloride (380 mg) and bromotrispyrrolidinophosphonium hexafluorophosphate (445 mg) were added and the reaction mixture was stirred at room temperature for 2 hours. Thereafter it was admixed with concentrated sodium hydrogencarbonate solution, and the aqueous phase was separated off and extracted with ethyl acetate. The combined organic phases were dried over sodium sulphate and concentrated. Purification by column chromatography gave N-(4-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3,5-difluorophenyl)methansulphonamide (255 mg).

$^1$H NMR (DMSO-$d_6$): 8.02 (s, 1H), 7.18 (t, 1H), 7.02 (t, 1H), 6.93-6.86 (m, 4H), 5.93 (dd, 1H), 5.43 (d, 1H), 5.35 (d, 1H), 4.40-4.32 (m, 1H), 4.01-3.95 (m, 1H), 3.83 (dd, 1H), 3.50 (dd, 1H), 3.45-3.35 (m, 1H), 3.35-3.24 (m, 1H), 3.14 (s, 3H), 2.89-2.80 (m, 1H), 2.16-2.05 (m, 2H), 1.86-1.75 (m, 1H), 1.63-1.50 (m, 1H)

Preparation of Compound XIV-1

[3,5-Bis(difluoromethyl)-1H-pyrazol-1-yl]acetyl fluoride (XIV-1)

A solution of [3,5-bis(difluoromethyl)-1H-pyrazol-1-yl]acetic acid (1.0 g) and pyridine (0.35 g) in dichloromethane (10 mL) was admixed at 0° C. with 2,4,6-trifluoro-1,3,5-triazine (0.60 g). After stirring overnight at 20° C., the reaction mixture was admixed with cyclohexane (10 mL) and filtered. The filtrate was concentrated under reduced pressure. This gave [3,5-bis(difluoromethyl)-1H-pyrazol-1-yl]acetyl fluoride (1.1 g).

$^1$H NMR (600 MHz, CDCl$_3$): $\delta_{ppm}$: 6.80 (s, 1H), 6.79 (t, 1H, J=53.6 Hz), 6.68 (t, 1H, J=54.7 Hz), 5.28 (d, 2H, J=4.3 Hz).

$^{19}$F NMR (566 MHz, CDCl$_3$): $\delta_{ppm}$: 32.7 (t, J=4.5 Hz), −113.3 (d, J=53.3 Hz), −113.5 (d, J=54.6 Hz).

The following compounds can be prepared using one or more of the processes specified above:

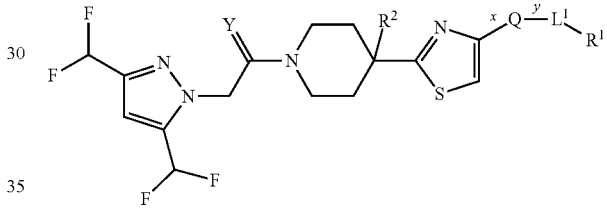

(I)

The structural element Q-3 listed in Table 1 is defined as follows:

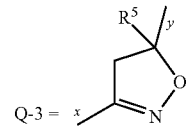

TABLE 1

For all of the compounds listed in Table 1, $L^1$ is a direct bond.

| Ex. | Y | $R^2$ | Q | $R^5$ | $R^1$ | LogP |
|---|---|---|---|---|---|---|
| I-1 | O | H | Q- | CH$_3$ | 4,5-dimethyl-2-(prop-2-yn-1-yloxy)phenyl | 4.1$^{[a]}$; 4.04$^{[b]}$ |
| I-2 | O | H | Q- | H | 2,6-difluoro-3-(prop-2-yn-1-yloxy)phenyl | 3.26$^{[a]}$; 3.18$^{[b]}$ |
| I-3 | O | H | Q- | H | 2,6-difluoro-4-(prop-2-yn-1-yloxy)phenyl | 3.3$^{[a]}$; 3.26$^{[b]}$ |
| I-4 | O | H | Q- | H | 3-(allyloxy)-2,6-difluorophenyl | 3.59$^{[a]}$; 3.51$^{[b]}$ |
| I-5 | O | H | Q- | H | 2,6-difluoro-4-[(methylsulphonyl)amino]phenyl | 2.63$^{[a]}$ |
| I-6 | O | H | Q- | H | 6-{[(2Z)-3-chloroprop-2-en-1-yl]oxy}-2,3-difluorophenyl | 3.79$^{[a]}$; 3.71$^{[b]}$ |
| I-7 | O | H | Q- | H | 6-[(2-chloroprop-2-en-1-yl)oxy]-2,3-difluorophenyl | 3.68$^{[a]}$; 3.69$^{[b]}$ |
| I-8 | O | H | Q- | H | 2,3-difluoro-6-(prop-2-yn-1-yloxy)phenyl | 3.3$^{[a]}$; 3.27$^{[b]}$ |
| I-9 | O | H | Q- | H | 4-[(cyclopropylcarbonyl)oxy]-2,6-difluorophenyl | 3.53$^{[a]}$ |
| I-10 | O | H | Q- | H | 3,5-difluoro-2-(prop-2-yn-1-yloxy)phenyl | 3.58$^{[a]}$; 3.51$^{[b]}$ |
| I-11 | O | H | Q- | H | 4-(allyloxy)-2,6-difluorophenyl | 3.7$^{[a]}$ |
| I-12 | O | H | Q- | H | 3,6-difluoro-2-(prop-2-yn-1-yloxy)phenyl | 3.31$^{[a]}$; 3.3$^{[b]}$ |
| I-13 | O | H | Q- | H | 2,4-difluoro-6-(prop-2-yn-1-yloxy)phenyl | 3.32$^{[a]}$ |
| I-14 | O | H | Q- | H | 2,6-difluoro-4-formylphenyl | 2.93$^{[a]}$; 2.87$^{[b]}$ |
| I-15 | O | H | Q- | H | 2-(cyclopropylmethoxy)-4,6-difluorophenyl | 3.81$^{[a]}$; 3.76$^{[b]}$ |

TABLE 1-continued

For all of the compounds listed in Table 1, $L^1$ is a direct bond.

| Ex. | Y | $R^2$ | Q | $R^5$ | $R^1$ | LogP |
|---|---|---|---|---|---|---|
| I-16 | O | H | Q- | H | 2-[(cyclopropylcarbonyl)oxy]-4,6-difluorophenyl | 3.5[a]; 3.42[b] |
| I-17 | O | H | Q- | H | 6-(allyloxy)-2,3-difluorophenyl | 3.53[a]; 3.56[b] |
| I-18 | O | H | Q- | H | 2-(allyloxy)-4,6-dichlorophenyl | 4.29[a]; 4.2[b] |
| I-19 | O | H | Q- | H | 2-[(2-chloroprop-2-en-1-yl)oxy]-4,6-difluorophenyl | 3.79[a]; 3.7[b] |
| I-20 | O | H | Q- | H | 2-(allyloxy)-4,6-difluorophenyl | 3.67[a]; 3.58[b] |
| I-21 | O | H | Q- | H | 2,4-dichloro-6-(prop-2-yn-1-yloxy)phenyl | 3.94[a]; 3.85[b] |

The logP values were determined in accordance with EEC Directive 79/831 Annex V.A8 by HPLC (High Performance Liquid Chromatography) on reversed-phase columns (C 18), using the methods below:
[a]Determination by LC-MS in the acidic range takes place at pH 2.7 using 0.1% aqueous formic acid and acetonitrile (containing 0.1% formic acid) as eluents; linear gradient from 10% acetonitrile to 95% acetonitrile
[b]Determination by LC-MS in the neutral range takes place at pH 7.8 using 0.001 molar aqueous ammonium hydrogencarbonate solution and acetonitrile as eluents; linear gradient from 10% acetonitrile to 95% acetonitrile.

Calibration takes place using unbranched alkan-2-ones (having 3 to 16 carbon atoms) whose log P values are known (log P values determined on the basis of the retention times, by linear interpolation between two successive alkanones).

The lambda-max values were determined by means of the UV spectra from 200 nm to 400 nm in the maxima of the chromatographic signals.

NMR Data of Selected Examples

NMR Peak List Method

The 1H-NMR data of Examples I-2 to I-21 are recorded in the form of $^1$H-NMR peak lists. For each signal peak, the δ value in ppm and the signal intensity are listed in brackets:

Example I-2, solvent: DMSO-$d_6$, spectrometer: 399.95 MHz 8.0321 (10.80); 7.3369 (0.68); 7.3244 (0.70); 7.3139 (2.93); 7.3007 (1.44); 7.2901 (0.83); 7.2775 (0.83); 7.1806 (3.49); 7.1669 (1.70); 7.1516 (0.99); 7.1269 (1.61); 7.1079 (0.75); 7.1032 (0.78); 7.0475 (1.68); 7.0309 (4.13); 6.9059 (3.38); 6.8950 (2.03); 6.0178 (1.09); 5.9964 (1.30); 5.9872 (1.32); 5.9660 (1.19); 5.7554 (16.00); 5.4601 (0.75); 5.4189 (2.59); 5.3772 (2.57); 5.3351 (0.73); 4.8979 (7.50); 4.8919 (7.68); 4.3728 (0.77); 4.3379 (0.85); 4.0558 (0.51); 4.0379 (1.27); 4.0201 (1.38); 4.0025 (0.71); 3.9879 (0.70); 3.9553 (0.82); 3.9404 (0.94); 3.9099 (0.97); 3.8963 (1.14); 3.8672 (0.97); 3.6460 (2.31); 3.6401 (5.32); 3.6342 (2.33); 3.5740 (1.23); 3.5530 (1.15); 3.5309 (0.98); 3.5097 (1.00); 3.4298 (0.59); 3.4104 (0.63); 3.4014 (1.14); 3.3913 (0.72); 3.3821 (0.52); 3.3724 (0.63); 3.3642 (0.52); 3.3217 (441.54); 3.2982 (2.78); 3.2716 (1.08); 3.2428 (0.61); 2.8745 (0.55); 2.8477 (0.91); 2.8146 (0.55); 2.6748 (0.82); 2.6700 (1.07); 2.6655 (0.76); 2.5405 (0.58); 2.5236 (1.67); 2.5190 (2.60); 2.5055 (115.26); 2.5013 (157.77); 2.4975 (107.29); 2.3326 (0.84); 2.3278 (1.12); 2.3233 (0.82); 2.3191 (0.43); 2.1488 (0.67); 2.1166 (1.32); 2.0734 (1.55); 1.9884 (6.00); 1.8249 (0.63); 1.8037 (0.58); 1.5985 (0.66); 1.5885 (0.60); 1.5672 (0.59); 1.5566 (0.60); 1.2350 (0.58); 1.1922 (1.60); 1.1744 (3.24); 1.1567 (1.56); 0.0079 (0.44); −0.0002 (14.13); −0.0084 (0.43)

Example I-3, solvent: DMSO-$d_6$, spectrometer: 399.95 MHz 8.0257 (0.56); 8.0121 (14.18); 7.3097 (2.42); 7.1764 (5.60); 7.1594 (2.69); 7.0432 (2.77); 7.0234 (6.20); 6.9003 (5.53); 6.8875 (3.27); 6.8811 (0.99); 6.8646 (6.62); 6.8384 (6.44); 5.9498 (1.71); 5.9284 (2.08); 5.9200 (1.97); 5.8983 (1.73); 5.4549 (1.09); 5.4121 (4.09); 5.3707 (4.02); 5.3284 (1.08); 4.8880 (11.02); 4.8821 (10.88); 4.3687 (1.26); 4.3370 (1.29); 3.9899 (1.20); 3.9563 (1.33); 3.8847 (1.37); 3.8543 (1.59); 3.8417 (1.88); 3.8114 (1.63); 3.6502 (3.01); 3.6443 (6.39); 3.6384 (2.86); 3.5314 (2.07); 3.5099 (2.15); 3.4880 (1.76); 3.4667 (1.80); 3.4363 (0.86); 3.4267 (1.28); 3.4173 (1.10); 3.4074 (1.56); 3.3983 (2.36); 3.3891 (1.73); 3.3782 (1.53); 3.3699 (2.00); 3.3592 (2.01); 3.3112 (736.95); 3.2456 (1.13); 2.8770 (0.87); 2.8500 (1.54); 2.8200 (0.87); 2.6741 (0.41); 2.6696 (0.54); 2.6654 (0.38); 2.5395 (0.76); 2.5094 (30.86); 2.5050 (57.09); 2.5006 (74.10); 2.4962 (51.38); 2.4918 (24.73); 2.3315 (0.34); 2.3272 (0.49); 2.3229 (0.36); 2.1495 (1.13); 2.1167 (2.29); 2.0808 (1.54); 2.0691 (16.00); 1.8528 (0.45); 1.8236 (1.01); 1.8000 (0.93); 1.7702 (0.38); 1.7632 (0.34); 1.6214 (0.47); 1.5997 (0.97); 1.5913 (1.01); 1.5709 (0.96); 1.5611 (0.92); 1.5416 (0.37); 0.0078 (0.32); −0.0002 (6.83)

Example I-4, solvent: DMSO-$d_6$, spectrometer: 399.95 MHz 8.0312 (10.33); 7.3143 (1.44); 7.2692 (0.57); 7.2561 (0.63); 7.2458 (1.27); 7.2329 (1.25); 7.2224 (0.78); 7.2094 (0.71); 7.1810 (3.32); 7.1672 (1.60); 7.1051 (0.87); 7.1005 (0.94); 7.0802 (1.40); 7.0766 (1.41); 7.0572 (0.73); 7.0524 (0.84); 7.0479 (1.67); 7.0312 (3.91); 6.9064 (3.12); 6.8954 (1.86); 6.0697 (0.49); 6.0563 (1.11); 6.0433 (1.03); 6.0301 (1.28); 6.0266 (0.69); 6.0133 (2.08); 6.0000 (1.33); 5.9942 (1.33); 5.9867 (2.19); 5.9736 (0.69); 5.9638 (1.12); 5.7558 (1.84); 5.4616 (0.69); 5.4271 (0.99); 5.4229 (3.18); 5.4189 (4.51); 5.3797 (3.63); 5.3758 (3.65); 5.3350 (0.69); 5.2961 (0.77); 5.2927 (1.94); 5.2887 (1.84); 5.2852 (0.76); 5.2699 (0.71); 5.2664 (1.77); 5.2623 (1.75); 5.2589 (0.70); 4.6453 (2.25); 4.6418 (3.99); 4.6381 (2.46); 4.6320 (2.37); 4.6284 (3.90); 4.6248 (2.29); 4.3719 (0.65); 4.3384 (0.68); 4.0558 (1.12); 4.0380 (3.54); 4.0202 (3.59); 4.0024 (1.44); 3.9916 (0.61); 3.9562 (0.68); 3.9382 (0.84); 3.9073 (0.86); 3.8947 (1.02); 3.8642 (0.88); 3.5690 (1.09); 3.5475 (1.13); 3.5255 (0.88); 3.5047 (0.91); 3.4294 (0.49); 3.4199 (0.33); 3.4101 (0.57); 3.4006 (1.03); 3.3915 (0.59); 3.3812 (0.37); 3.3717 (0.54); 3.3202 (94.97); 3.2965 (1.30); 3.2724 (0.86); 3.2432 (0.46); 2.8725 (0.46); 2.8451 (0.80); 2.8157 (0.47); 2.6704 (0.37); 2.5236 (0.61); 2.5055 (38.05); 2.5014 (52.03); 2.4980 (35.04); 2.3283 (0.36); 2.1482 (0.62); 2.1156 (1.18); 2.0738 (1.25); 1.9885 (16.00); 1.8250 (0.57); 1.8014 (0.47); 1.5985 (0.51); 1.5902 (0.56); 1.5692 (0.49); 1.5590 (0.49); 1.3975 (0.53); 1.1923 (4.37); 1.1745 (8.84); 1.1567 (4.26); −0.0002 (7.40)

Example I-5, solvent: DMSO-$d_6$, spectrometer: 399.95 MHz 10.3937 (2.73); 8.0149 (6.46); 7.3095 (1.10); 7.1762 (2.52); 7.1592 (1.22); 7.0429 (1.25); 7.0232 (2.80); 7.0162 (0.51); 6.9086 (3.56); 6.9007 (3.11); 6.8869 (2.75); 6.8831 (3.38); 5.9564 (0.78); 5.9351 (0.93);

-continued 5.9266 (0.88); 5.9049 (0.77); 5.7461 (8.38); 5.4548 (0.51); 5.4119 (1.88); 5.3707 (1.85); 5.3286 (0.49); 5.2173 (0.66); 4.3698 (0.58); 4.3367 (0.63); 4.0394 (0.49); 4.0215 (0.51); 4.0036 (0.40); 3.9908 (0.58); 3.9571 (0.63); 3.8970 (0.62); 3.8666 (0.73); 3.8538 (0.83); 3.8235 (0.73); 3.6198 (0.46); 3.5323 (0.94); 3.5226 (0.46); 3.5106 (1.09); 3.4889 (1.05); 3.4768 (0.42); 3.4748 (0.43); 3.4670 (0.89); 3.4256 (0.57); 3.4153 (0.49); 3.4058 (0.71); 3.3971 (1.06); 3.3875 (0.76); 3.3777 (0.67); 3.3683 (0.86); 3.3590 (0.78); 3.3090 (218.66); 3.2819 (1.10); 3.2761 (1.07); 3.2468 (0.52); 3.1407 (16.00); 2.8775 (0.41); 2.8494 (0.74); 2.8194 (0.41); 2.5396 (0.62); 2.5226 (1.59); 2.5093 (17.23); 2.5050 (31.09); 2.5006 (39.79); 2.4961 (27.48); 2.4918 (13.07); 2.1486 (0.52); 2.1151 (1.07); 2.0790 (0.63); 2.0693 (0.52); 1.9868 (1.93); 1.8278 (0.50); 1.8134 (0.48); 1.7954 (0.68); 1.5986 (0.46); 1.5916 (0.47); 1.5698 (0.45); 1.5604 (0.43); 1.1928 (0.54); 1.1750 (1.06); 1.1572 (0.53); −0.0002 (0.95)
Example I-6, solvent: DMSO-$d_6$, spectrometer: 399.95 MHz 7.9865 (12.73); 7.4770 (0.88); 7.4536 (2.07); 7.4284 (2.11); 7.4049 (0.93); 7.3138 (1.89); 7.1805 (4.51); 7.1668 (2.14); 7.0473 (2.15); 7.0308 (5.13); 6.9673 (1.06); 6.9630 (1.28); 6.9583 (1.21); 6.9539 (1.18); 6.9434 (1.04); 6.9395 (1.23); 6.9348 (1.17); 6.9312 (1.07); 6.9067 (4.30); 6.8950 (2.49); 6.4336 (1.25); 6.4298 (2.53); 6.4261 (1.30); 6.4156 (1.38); 6.4118 (2.74); 6.4081 (1.39); 6.0897 (1.48); 6.0692 (1.75); 6.0590 (1.68); 6.0383 (1.56); 6.0267 (1.22); 6.0116 (2.85); 5.9938 (2.68); 5.9788 (1.20); 5.7560 (16.00); 5.4656 (1.01); 5.4230 (3.22); 5.3782 (3.16); 5.3354 (1.00); 4.7347 (3.65); 4.7316 (4.12); 4.7169 (4.02); 4.3738 (0.89); 4.3407 (0.94); 4.0378 (0.69); 4.0200 (0.72); 4.0020 (0.67); 3.9922 (0.83); 3.9580 (0.92); 3.8464 (1.14); 3.8155 (1.36); 3.8037 (1.67); 3.7729 (1.44); 3.5679 (0.36); 3.5502 (1.68); 3.5296 (1.71); 3.5072 (1.32); 3.4868 (1.33); 3.4275 (0.62); 3.4180 (0.45); 3.4081 (0.77); 3.3988 (1.40); 3.3895 (0.78); 3.3792 (0.48); 3.3700 (0.73); 3.3609 (0.37); 3.3213 (83.38); 3.2737 (1.22); 3.2451 (0.69); 2.8745 (0.62); 2.8437 (1.12); 2.8171 (0.63); 2.6751 (0.50); 2.6706 (0.74); 2.6660 (0.51); 2.5240 (1.60); 2.5192 (2.57); 2.5106 (41.11); 2.5060 (85.13); 2.5014 (115.73); 2.4968 (85.95); 2.4923 (41.91); 2.3328 (0.61); 2.3282 (0.83); 2.3236 (0.62); 2.3192 (0.32); 2.1487 (0.80); 2.1153 (1.65); 2.0803 (0.94); 1.9886 (3.13); 1.8525 (0.36); 1.8236 (0.73); 1.7978 (0.66); 1.6205 (0.39); 1.6002 (0.74); 1.5907 (0.81); 1.5690 (0.76); 1.5597 (0.72); 1.3357 (0.59); 1.2495 (0.76); 1.1926 (0.85); 1.1747 (1.66); 1.1569 (0.83); 0.0080 (0.64); −0.0002 (22.05); −0.0085 (0.77)
Example I-7, solvent: DMSO-$d_6$, spectrometer: 399.95 MHz 8.3197 (0.65); 7.9856 (16.00); 7.4879 (1.28); 7.4644 (3.23); 7.4397 (3.13); 7.4160 (1.28); 7.3159 (2.66); 7.1826 (6.57); 7.1704 (3.06); 7.0494 (3.14); 7.0344 (6.91); 6.9987 (2.18); 6.9945 (2.47); 6.9900 (2.30); 6.9858 (2.03); 6.9749 (2.08); 6.9710 (2.29); 6.9668 (2.05); 6.9098 (7.03); 6.8986 (3.50); 6.1198 (2.17); 6.0971 (2.92); 6.0893 (2.52); 6.0669 (2.22); 5.7601 (15.24); 5.7022 (6.95); 5.6982 (6.18); 5.4683 (1.85); 5.4435 (8.54); 5.4390 (7.51); 5.4259 (5.36); 5.3797 (5.13); 5.3376 (1.75); 4.7945 (0.61); 4.7599 (13.49); 4.7241 (0.57); 4.5089 (0.84); 4.3691 (1.76); 4.3361 (1.83); 4.0372 (0.41); 4.0193 (0.46); 3.9893 (1.65); 3.9549 (1.79); 3.8680 (1.68); 3.8370 (2.07); 3.8253 (2.53); 3.7948 (2.21); 3.6188 (2.59); 3.5964 (2.61); 3.5759 (2.01); 3.5680 (1.20); 3.5537 (1.89); 3.4233 (1.18); 3.4140 (0.90); 3.4038 (1.53); 3.3950 (2.36); 3.3857 (1.44); 3.3749 (1.05); 3.3665 (1.44); 3.3563 (1.20); 3.3373 (20.72); 3.3328 (81.37); 3.3044 (1.38); 3.2731 (2.25); 3.2435 (1.28); 2.8904 (0.72); 2.8787 (1.07); 2.8742 (1.11); 2.8464 (2.18); 2.8161 (1.20); 2.7311 (0.42); 2.6759 (1.60); 2.6714 (1.91); 2.6669 (1.28); 2.5525 (2.03); 2.5110 (150.43); 2.5068 (249.11); 2.5023 (291.51); 2.4978 (204.83); 2.4936 (95.93); 2.3336 (1.86); 2.3291 (2.17); 2.3246 (1.56); 2.1444 (1.65); 2.1092 (3.36); 2.0752 (1.93); 1.9895 (1.78); 1.8551 (0.64); 1.8473 (0.72); 1.8253 (1.47); 1.8186 (1.49); 1.7956 (1.45); 1.7886 (1.29); 1.7657 (0.59); 1.6238 (0.64); 1.6127 (0.73); 1.5921 (1.48); 1.5832 (1.50); 1.5615 (1.49); 1.5530 (1.34); 1.5312 (0.61); 1.5218 (0.48); 1.3359 (2.56); 1.2980 (0.76); 1.2724 (0.37); 1.2582 (1.31); 1.2492 (3.17); 1.2351 (1.08); 1.1924 (0.61); 1.1746 (1.01); 1.1568 (0.58); 1.1377 (4.64); −0.0002 (36.52); −0.0085 (1.51)
Example I-8, solvent: DMSO-$d_6$, spectrometer: 399.95 MHz 7.9923 (11.58); 7.5087 (0.95); 7.4851 (2.36); 7.4605 (2.36); 7.4368 (0.95); 7.3140 (2.05); 7.1807 (4.71); 7.1670 (2.23); 7.0475 (2.29); 7.0310 (5.16); 7.0094 (1.55); 7.0048 (1.49); 7.0007 (1.43); 6.9860 (1.44); 6.9814 (1.34); 6.9059 (4.88); 6.8952 (2.64); 6.0729 (1.55); 6.0513 (1.86); 6.0426 (1.81); 6.0207 (1.62); 5.4625 (1.15); 5.4198 (3.83); 5.3779 (3.79); 5.3355 (1.14); 4.8879 (0.34); 4.8822 (0.35); 4.8478 (5.13); 4.8424 (8.89); 4.8371 (5.16); 4.8027 (0.36); 4.7968 (0.36); 4.3709 (1.11); 4.3372 (1.16); 3.9904 (1.04); 3.9561 (1.14); 3.9024 (16.00); 3.8624 (1.24); 3.8316 (1.41); 3.8195 (1.76); 3.7890 (1.54); 3.5683 (1.93); 3.5598 (2.71); 3.5539 (5.68); 3.5479 (4.11); 3.5256 (1.47); 3.5039 (1.45); 3.4343 (0.46); 3.4255 (0.76); 3.4159 (0.55); 3.4058 (0.92); 3.3968 (1.60); 3.3877 (0.94); 3.3774 (0.60); 3.3683 (0.86); 3.3596 (0.46); 3.3186 (55.10); 3.2727 (1.45); 3.2440 (0.80); 3.1746 (0.48); 3.1613 (0.45); 2.8903 (0.54); 2.8737 (0.78); 2.8443 (1.41); 2.8166 (0.78); 2.7310 (0.35); 2.6746 (1.14); 2.6702 (1.58); 2.6658 (1.17); 2.5233 (4.73); 2.5098 (90.48); 2.5056 (178.21); 2.5011 (234.80); 2.4967 (174.33); 2.3322 (1.22); 2.3279 (1.65); 2.3236 (1.24); 2.1526 (1.00); 2.1168 (2.04); 2.0816 (1.16); 1.8585 (0.35); 1.8532 (0.40); 1.8230 (0.91); 1.8004 (0.84); 1.7934 (0.81); 1.7711 (0.33); 1.6310 (0.35); 1.6204 (0.44); 1.5994 (0.89); 1.5901 (0.95); 1.5693 (0.91); 1.5596 (0.86); 1.5389 (0.36); 1.3353 (0.41); 1.2585 (0.38); 1.2494 (0.45); 0.0078 (1.46); −0.0002 (41.84); −0.0082 (1.76)
Example I-9, solvent: DMSO-$d_6$, spectrometer: 399.95 MHz 8.0348 (8.87); 7.3148 (1.29); 7.1815 (3.16); 7.1683 (2.30); 7.1628 (4.01); 7.1401 (3.74); 7.0484 (1.47); 7.0323 (3.61); 6.9072 (2.88); 6.8965 (1.74); 6.0081 (0.88); 5.9872 (1.05); 5.9779 (0.99); 5.9568 (0.90); 5.4627 (0.64); 5.4200 (2.17); 5.3784 (2.16); 5.3358 (0.63); 4.3701 (0.59); 4.3378 (0.63); 4.0554 (1.15); 4.0376 (3.55); 4.0199 (3.60); 4.0020 (1.43); 3.9900 (0.57); 3.9565 (0.68); 3.9330 (0.73); 3.9024 (0.78); 3.8895 (0.92); 3.8592 (0.79); 3.5813 (0.98); 3.5601 (1.01); 3.5377 (0.80); 3.5168 (0.80); 3.4290 (0.45); 3.4199 (0.33); 3.4099 (0.53); 3.4002 (0.91); 3.3915 (0.53); 3.3806 (0.35); 3.3715 (0.50); 3.3228 (57.43); 3.3007 (0.52); 3.2708 (0.80); 3.2420 (0.47); 2.8710 (0.44); 2.8399 (0.76); 2.8133 (0.45); 2.6749 (0.37); 2.6704 (0.55); 2.6658 (0.39); 2.5646 (2.25); 2.5238 (1.62); 2.5191 (2.42); 2.5104 (30.49); 2.5059 (62.12); 2.5013 (81.90); 2.4967 (57.90); 2.4921 (27.04); 2.3328 (0.38); 2.3280 (0.53); 2.3236 (0.38); 2.1485 (0.60); 2.1144 (1.09); 2.0794 (0.63); 1.9887 (16.00); 1.9330 (0.43); 1.9211 (0.85); 1.9135 (1.00);

-continued 1.9086 (2.86); 1.9018 (1.61); 1.8967 (0.73); 1.8899 (0.90); 1.8823 (0.95); 1.8706 (0.55); 1.8253 (0.56); 1.8002 (0.44); 1.7957 (0.44); 1.5956 (0.47); 1.5870 (0.52); 1.5656 (0.51); 1.5570 (0.46); 1.4058 (0.78); 1.3974 (5.11); 1.1922 (4.31); 1.1744 (8.70); 1.1566 (4.21); 1.1187 (0.45); 1.1048 (1.62); 1.0972 (3.04); 1.0912 (1.62); 1.0848 (1.50); 1.0770 (2.88); 1.0711 (1.55); 1.0654 (1.93); 1.0594 (2.95); 1.0520 (2.63); 1.0484 (3.15); 1.0404 (1.61); 1.0266 (0.36); 0.0080 (0.85); −0.0002 (28.40); −0.0086 (0.84)
Example I-10, solvent: DMSO-$d_6$, spectrometer: 399.95 MHz 8.0353 (13.66); 7.3972 (1.40); 7.3896 (1.42); 7.3756 (1.54); 7.3683 (2.73); 7.3609 (1.53); 7.3470 (1.47); 7.3393 (1.44); 7.3116 (2.43); 7.1783 (5.57); 7.1667 (2.71); 7.0451 (2.71); 7.0306 (6.11); 7.0162 (1.67); 7.0119 (2.00); 6.9936 (1.71); 6.9894 (2.02); 6.9060 (5.82); 6.8949 (3.16); 5.9853 (1.96); 5.9667 (2.25); 5.9576 (2.25); 5.9386 (2.03); 5.7558 (16.00); 5.4588 (1.35); 5.4163 (4.61); 5.3744 (4.56); 5.3320 (1.37); 4.8270 (11.86); 4.8210 (12.23); 4.3634 (1.35); 4.3305 (1.41); 4.0559 (0.33); 4.0381 (1.05); 4.0203 (1.08); 4.0024 (0.49); 3.9789 (3.26); 3.9506 (3.67); 3.9355 (3.34); 3.9074 (2.39); 3.6710 (2.94); 3.6650 (6.17); 3.6591 (3.10); 3.4209 (0.46); 3.4119 (1.00); 3.4034 (3.18); 3.3928 (1.31); 3.3844 (4.34); 3.3746 (1.26); 3.3601 (2.86); 3.3415 (2.65); 3.3199 (50.52); 3.2951 (1.12); 3.2646 (1.78); 3.2360 (0.96); 2.8658 (0.92); 2.8357 (1.68); 2.8080 (0.94); 2.6753 (0.56); 2.6708 (0.81); 2.6663 (0.59); 2.5239 (1.87); 2.5061 (95.77); 2.5017 (127.50); 2.4973 (96.60); 2.3328 (0.71); 2.3284 (0.93); 2.3244 (0.73); 2.1327 (1.21); 2.0977 (2.49); 2.0642 (1.40); 1.9888 (4.60); 1.8479 (0.44); 1.8397 (0.53); 1.8172 (1.06); 1.8094 (1.17); 1.7867 (1.07); 1.7793 (1.01); 1.7572 (0.43); 1.7477 (0.36); 1.6139 (0.44); 1.6032 (0.54); 1.5828 (1.08); 1.5730 (1.18); 1.5519 (1.10); 1.5432 (1.07); 1.5222 (0.45); 1.5115 (0.37); 1.3360 (0.93); 1.2589 (0.38); 1.2497 (1.07); 1.1927 (1.23); 1.1749 (2.39); 1.1571 (1.19); 0.0079 (1.10); −0.0002 (34.59); −0.0083 (1.46)
Example I-11, solvent: DMSO-$d_6$, spectrometer: 399.95 MHz 8.3939 (0.50); 8.0195 (16.00); 7.9523 (0.43); 7.4270 (0.41); 7.3150 (2.46); 7.1818 (5.77); 7.1688 (2.91); 7.0763 (0.46); 7.0486 (2.82); 7.0327 (6.70); 6.9974 (0.36); 6.9076 (5.75); 6.8969 (3.38); 6.8441 (0.70); 6.8286 (7.12); 6.8019 (7.15); 6.7866 (0.69); 6.0632 (0.73); 6.0499 (1.21); 6.0368 (1.58); 6.0236 (1.93); 6.0203 (1.13); 6.0103 (1.07); 6.0068 (2.10); 5.9936 (1.84); 5.9804 (2.08); 5.9672 (0.99); 5.9408 (1.78); 5.9193 (2.15); 5.9108 (2.09); 5.8891 (1.86); 5.7992 (1.11); 5.7576 (2.26); 5.7219 (0.52); 5.4631 (1.31); 5.4334 (1.52); 5.4295 (3.96); 5.4252 (5.07); 5.4210 (5.59); 5.3901 (1.56); 5.3863 (3.83); 5.3819 (5.52); 5.3785 (5.54); 5.3360 (1.31); 5.3035 (3.45); 5.2998 (3.48); 5.2772 (3.25); 5.2735 (3.25); 4.6353 (4.28); 4.6320 (7.26); 4.6285 (4.87); 4.6222 (4.70); 4.6187 (7.26); 4.6154 (4.55); 4.3715 (1.23); 4.3382 (1.30); 3.9892 (1.12); 3.9556 (1.26); 3.8790 (1.39); 3.8485 (1.60); 3.8358 (1.90); 3.8055 (1.66); 3.5154 (2.01); 3.4938 (2.07); 3.4721 (1.71); 3.4507 (1.68); 3.4357 (0.56); 3.4259 (0.94); 3.4170 (0.65); 3.4070 (1.06); 3.3974 (1.87); 3.3882 (1.10); 3.3784 (0.70); 3.3689 (0.99); 3.3600 (0.53); 3.3216 (94.65); 3.3001 (1.16); 3.2701 (1.67); 3.2420 (0.96); 2.9375 (0.93); 2.8901 (3.73); 2.8699 (0.86); 2.8396 (1.55); 2.8124 (0.91); 2.7305 (2.82); 2.6806 (2.46); 2.6749 (1.31); 2.6703 (1.75); 2.6658 (1.24); 2.6613 (0.53); 2.5236 (4.85); 2.5188 (8.09); 2.5102 (103.54); 2.5058 (208.03); 2.5012 (273.59); 2.4966 (198.03); 2.4922 (95.51); 2.3368 (0.75); 2.3325 (1.46); 2.3280 (1.96); 2.3234 (1.45); 2.3189 (0.76); 2.1470 (1.16); 2.1136 (2.34); 2.0789 (1.38); 1.8599 (0.46); 1.8503 (0.52); 1.8291 (1.01); 1.8214 (1.09); 1.7996 (0.98); 1.7908 (0.96); 1.7681 (0.43); 1.7594 (0.37); 1.6241 (0.42); 1.6153 (0.51); 1.5939 (1.01); 1.5854 (1.07); 1.5641 (1.01); 1.5546 (0.98); 1.5333 (0.44); 1.5239 (0.37); 1.2980 (0.56); 1.2584 (0.78); 1.2440 (0.42); 1.2339 (0.76); 0.1460 (0.65); 0.0079 (5.35); −0.0002 (159.14); −0.0084 (5.61); −0.0257 (0.38); −0.1497 (0.74)
Example I-12, solvent: DMSO-$d_6$, spectrometer: 399.95 MHz 8.3156 (0.33); 8.0077 (16.00); 7.4387 (1.52); 7.4260 (1.68); 7.4151 (2.11); 7.4120 (2.17); 7.4026 (2.14); 7.3994 (2.09); 7.3885 (1.82); 7.3758 (1.70); 7.3139 (2.92); 7.1807 (6.72); 7.1670 (3.26); 7.1336 (1.78); 7.1240 (1.88); 7.1094 (3.00); 7.0999 (2.97); 7.0856 (1.57); 7.0760 (1.49); 7.0475 (3.26); 7.0310 (7.20); 6.9065 (7.33); 6.8952 (3.87); 6.0606 (2.42); 6.0386 (2.92); 6.0303 (2.91); 6.0080 (2.54); 5.7560 (14.97); 5.4622 (1.70); 5.4196 (5.76); 5.3789 (5.65); 5.3363 (1.70); 4.8734 (1.67); 4.8675 (1.74); 4.8338 (6.04); 4.8278 (6.33); 4.8069 (5.95); 4.8010 (6.17); 4.7673 (1.62); 4.7614 (1.70); 4.3729 (1.75); 4.3403 (1.83); 4.0557 (0.46); 4.0377 (1.38); 4.0200 (1.45); 4.0018 (1.23); 3.9905 (1.65); 3.9562 (1.41); 3.8923 (1.61); 3.8616 (1.83); 3.8493 (2.23); 3.8190 (1.99); 3.6461 (3.82); 3.6402 (7.80); 3.6344 (3.96); 3.5426 (2.60); 3.5205 (2.62); 3.4994 (2.11); 3.4773 (2.08); 3.4345 (0.61); 3.4251 (1.17); 3.4160 (0.87); 3.4059 (1.40); 3.3967 (2.42); 3.3875 (1.48); 3.3776 (0.95); 3.3680 (1.33); 3.3590 (0.78); 3.3215 (59.77); 3.2719 (2.28); 3.2428 (1.22); 2.8720 (1.21); 2.8417 (2.19); 2.8144 (1.19); 2.6748 (0.82); 2.6705 (1.24); 2.6663 (0.88); 2.5058 (134.11); 2.5015 (175.63); 2.4972 (134.47); 2.3325 (0.92); 2.3283 (1.21); 2.3240 (0.97); 2.1491 (1.57); 2.1174 (3.23); 2.0818 (1.82); 1.9886 (5.76); 1.8629 (0.53); 1.8532 (0.66); 1.8314 (1.37); 1.8234 (1.52); 1.8009 (1.38); 1.7939 (1.31); 1.7716 (0.56); 1.7624 (0.47); 1.6308 (0.54); 1.6211 (0.70); 1.6006 (1.39); 1.5915 (1.53); 1.5696 (1.41); 1.5605 (1.36); 1.5393 (0.57); 1.5295 (0.47); 1.3358 (1.19); 1.2587 (0.37); 1.2496 (1.37); 1.2350 (0.45); 1.1925 (1.51); 1.1747 (2.97); 1.1570 (1.49); 0.0076 (1.19); −0.0002 (27.94)
Example I-13, solvent: DMSO-$d_6$, spectrometer: 399.95 MHz 8.0230 (0.42); 7.9766 (16.00); 7.3166 (2.62); 7.1833 (6.21); 7.1710 (3.10); 7.0502 (2.99); 7.0350 (7.08); 6.9724 (2.47); 6.9639 (2.17); 6.9575 (1.34); 6.9533 (1.89); 6.9447 (3.17); 6.9407 (3.16); 6.9372 (2.49); 6.9312 (1.60); 6.9102 (7.04); 6.8992 (3.60); 6.0215 (1.98); 5.9995 (2.40); 5.9910 (2.30); 5.9689 (2.05); 5.7596 (15.20); 5.4664 (1.51); 5.4237 (4.78); 5.3813 (4.71); 5.3387 (1.51); 4.9285 (0.41); 4.9226 (0.44); 4.8885 (6.19); 4.8833 (10.07); 4.8781 (6.12); 4.8440 (0.57); 4.8380 (0.44); 4.7531 (0.84); 4.3724 (1.35); 4.3391 (1.46); 4.0553 (0.53); 4.0374 (1.61); 4.0196 (1.67); 4.0017 (1.10); 3.9905 (1.27); 3.9562 (1.41); 3.8062 (1.29); 3.7745 (1.53); 3.7621 (1.86); 3.7319 (1.69); 3.5810 (3.07); 3.5751 (6.98); 3.5692 (3.06); 3.5102 (2.15); 3.4879 (2.20); 3.4672 (1.67); 3.4454 (1.70); 3.4305 (0.52); 3.4212 (0.93); 3.4116 (0.68); 3.4016 (1.14); 3.3926 (1.94); 3.3832 (1.15); 3.3731 (0.76); 3.3638 (1.08); 3.3548 (0.70); 3.3343 (63.61); 3.3003 (1.10); 3.2705 (1.82); 3.2414 (1.04); 2.8702 (0.96); 2.8398 (1.75); 2.8129 (1.01); 2.6761 (0.45); 2.6715 (0.67); 2.6671 (0.49); 2.5250 (1.73); 2.5202 (2.87); 2.5115 (39.45); 2.5071 (80.45); 2.5025 (106.22); 2.4980 (78.38); 2.4936 (39.34); 2.3338 (0.58); 2.3292 (0.78); 2.3247 (0.60); 2.1497 (1.21); 2.1145 (2.50); 2.0789 (1.45); 1.9896 (7.28); 1.8580 (0.45); 1.8507 (0.53); 1.8215 (1.15); 1.7982 (1.07); 1.7910 (1.03); 1.7700 (0.44); 1.7606 (0.37); 1.6249 (0.44); 1.6157 (0.54); 1.5948 (1.09); 1.5856 (1.20); 1.5643 (1.14); 1.5556 (1.09); 1.5346 (0.49); 1.5240 (0.38); 1.3973 (0.86); 1.3364 (0.68); 1.2586 (0.37); 1.2495 (0.89); 1.2347 (0.54); 1.1924 (1.98); 1.1747 (3.96); 1.1568 (1.97); −0.0002 (5.11)

| Example I-14, solvent: DMSO-d$_6$, spectrometer: 399.95 MHz |
| --- |

9.9796 (4.86); 9.9008 (0.54); 8.6585 (0.57); 8.3154 (0.32); 8.0576 (10.91); 7.7244 (0.84); 7.7147 (5.87); 7.6945 (5.87); 7.6852 (0.93); 7.3144 (1.98); 7.1811 (4.70); 7.1668 (2.22); 7.0479 (2.24); 7.0307 (5.04); 6.9066 (4.74); 6.8949 (2.57); 6.0913 (1.41); 6.0706 (1.66); 6.0611 (1.62); 6.0401 (1.48); 5.7560 (16.00); 5.4629 (1.02); 5.4204 (3.52); 5.3792 (3.61); 5.3368 (1.08); 4.3743 (1.05); 4.3415 (1.09); 4.0557 (0.33); 4.0378 (1.00); 4.0199 (1.07); 3.9949 (2.01); 3.9647 (2.07); 3.9523 (2.36); 3.9215 (1.40); 3.6330 (1.57); 3.6121 (1.61); 3.5893 (1.31); 3.5684 (1.35); 3.4431 (0.37); 3.4337 (0.70); 3.4239 (0.52); 3.4143 (0.85); 3.4048 (1.46); 3.3953 (0.87); 3.3857 (0.56); 3.3763 (0.76); 3.3669 (0.42); 3.3219 (89.18); 3.2726 (1.41); 3.2440 (0.82); 2.8731 (0.73); 2.8420 (1.33); 2.8151 (0.76); 2.6751 (0.66); 2.6707 (0.94); 2.6662 (0.70); 2.5239 (2.72); 2.5104 (55.80); 2.5061 (112.26); 2.5017 (148.22); 2.4972 (109.34); 2.4928 (55.27); 2.3328 (0.76); 2.3284 (1.03); 2.3238 (0.79); 2.1512 (0.95); 2.1178 (1.95); 2.0830 (1.12); 1.9887 (4.39); 1.8568 (0.39); 1.8269 (0.85); 1.8049 (0.79); 1.6219 (0.41); 1.6006 (0.85); 1.5913 (0.88); 1.5703 (0.82); 1.5613 (0.78); 1.5409 (0.35); 1.3358 (1.70); 1.2983 (0.37); 1.2587 (0.54); 1.2496 (2.04); 1.2348 (0.55); 1.1926 (1.17); 1.1748 (2.28); 1.1570 (1.14); 0.0079 (0.70); −0.0002 (19.92); −0.0081 (0.85)

| Example I-15, solvent: DMSO-d$_6$, spectrometer: 399.95 MHz |
| --- |

7.9638 (16.00); 7.3135 (2.67); 7.1803 (6.33); 7.1676 (3.03); 7.0472 (3.06); 7.0317 (6.94); 6.9073 (6.53); 6.8959 (3.48); 6.8640 (1.24); 6.8580 (1.73); 6.8357 (7.52); 6.8101 (6.76); 6.0360 (2.24); 6.0152 (2.76); 6.0049 (2.58); 5.9840 (2.36); 5.4671 (1.70); 5.4252 (4.81); 5.3719 (4.71); 5.3290 (1.81); 4.3629 (1.49); 4.3316 (1.53); 4.0557 (0.64); 4.0378 (1.80); 4.0200 (1.88); 4.0024 (0.85); 3.9846 (1.39); 3.9500 (1.57); 3.9166 (2.34); 3.8997 (2.54); 3.8909 (3.26); 3.8741 (3.15); 3.7851 (1.73); 3.7600 (2.98); 3.7539 (2.55); 3.7418 (5.55); 3.7349 (2.71); 3.7145 (3.16); 3.5839 (2.65); 3.5629 (2.77); 3.5416 (1.93); 3.5208 (1.83); 3.4275 (0.70); 3.4181 (1.18); 3.4078 (0.90); 3.3984 (1.36); 3.3891 (2.37); 3.3808 (1.53); 3.3601 (2.29); 3.3507 (2.26); 3.3268 (446.42); 3.2902 (0.94); 3.2701 (2.16); 3.2422 (1.04); 2.8712 (1.05); 2.8397 (1.87); 2.8124 (1.08); 2.6752 (1.31); 2.6708 (1.75); 2.6662 (1.33); 2.5239 (5.68); 2.5105 (105.72); 2.5062 (210.23); 2.5017 (276.22); 2.4972 (205.17); 2.4929 (104.36); 2.3330 (1.29); 2.3285 (1.76); 2.3239 (1.28); 2.1225 (1.35); 2.0915 (2.77); 2.0560 (1.54); 2.0275 (0.42); 2.0086 (0.62); 1.9889 (8.29); 1.8299 (0.55); 1.8098 (1.17); 1.8016 (1.25); 1.7801 (1.15); 1.7723 (1.09); 1.7497 (0.44); 1.5959 (0.54); 1.5689 (1.19); 1.5437 (1.12); 1.5124 (0.46); 1.3977 (1.17); 1.3356 (1.03); 1.2943 (0.38); 1.2493 (2.29); 1.2363 (2.34); 1.1924 (2.17); 1.1746 (4.15); 1.1568 (2.07); 1.0059 (0.60); 0.9922 (1.19); 0.9876 (1.08); 0.9753 (1.81); 0.9571 (1.49); 0.9421 (0.72); 0.8542 (0.74); 0.8369 (0.33); 0.3767 (0.61); 0.3674 (0.77); 0.3551 (1.80); 0.3466 (1.68); 0.3368 (2.37); 0.3216 (1.21); 0.3159 (0.91); 0.2094 (0.37); 0.1899 (1.04); 0.1722 (2.53); 0.1621 (5.70); 0.1550 (4.79); 0.1489 (4.84); 0.1364 (3.36); 0.1256 (2.35); 0.1167 (1.24); 0.1082 (0.77); 0.0001 (2.70)

| Example I-16, solvent: DMSO-d$_6$, spectrometer: 399.95 MHz |
| --- |

8.0268 (14.48); 7.3244 (1.39); 7.3178 (1.71); 7.3125 (2.87); 7.3014 (1.80); 7.2963 (2.50); 7.2911 (1.80); 7.2746 (1.43); 7.2682 (1.44); 7.1792 (5.89); 7.1660 (2.94); 7.1548 (1.89); 7.1501 (2.49); 7.1451 (1.79); 7.1312 (1.92); 7.1266 (2.48); 7.0460 (2.81); 7.0300 (6.49); 6.9059 (6.08); 6.8942 (3.34); 5.8657 (2.07); 5.8437 (2.49); 5.8351 (2.47); 5.8129 (2.16); 5.7556 (16.00); 5.4644 (1.49); 5.4218 (4.55); 5.3742 (4.52); 5.3317 (1.50); 4.3690 (1.38); 4.3358 (1.47); 4.0555 (0.76); 4.0377 (2.35); 4.0199 (2.42); 4.0020 (1.15); 3.9874 (1.29); 3.9525 (1.45); 3.8976 (1.65); 3.8667 (1.92); 3.8542 (2.20); 3.8235 (1.89); 3.4337 (2.66); 3.4236 (1.21); 3.4118 (2.82); 3.4048 (1.49); 3.3907 (2.94); 3.3679 (2.77); 3.3577 (0.78); 3.3217 (65.27); 3.2691 (1.83); 3.2411 (0.99); 3.1182 (0.41); 2.8695 (0.96); 2.8392 (1.76); 2.8121 (1.03); 2.6749 (0.55); 2.6704 (0.80); 2.6660 (0.60); 2.5237 (2.14); 2.5099 (45.65); 2.5058 (91.16); 2.5014 (120.94); 2.4969 (90.89); 2.4926 (47.44); 2.3326 (0.61); 2.3282 (0.85); 2.3237 (0.65); 2.1379 (1.22); 2.1042 (2.59); 2.0695 (1.44); 1.9885 (10.15); 1.8510 (0.44); 1.8412 (0.52); 1.8204 (1.09); 1.8118 (1.19); 1.7899 (1.09); 1.7821 (1.04); 1.7608 (0.45); 1.7493 (0.40); 1.7424 (0.76); 1.7308 (1.41); 1.7226 (1.67); 1.7113 (2.97); 1.6999 (1.82); 1.6914 (1.68); 1.6799 (0.84); 1.6159 (0.42); 1.6054 (0.51); 1.5841 (1.07); 1.5750 (1.17); 1.5539 (1.08); 1.5451 (1.06); 1.5235 (0.44); 1.5176 (0.40); 1.3357 (1.04); 1.2495 (1.26); 1.1925 (2.72); 1.1748 (5.43); 1.1569 (2.68); 1.0448 (0.33); 1.0350 (0.92); 1.0210 (1.53); 1.0161 (1.70); 1.0112 (1.94); 1.0000 (3.16); 0.9909 (2.45); 0.9814 (3.03); 0.9739 (1.47); 0.9618 (1.29); 0.9528 (0.84); 0.9322 (0.97); 0.9222 (1.68); 0.9119 (1.46); 0.9067 (1.74); 0.8957 (1.71); 0.8891 (1.79); 0.8813 (1.66); 0.8701 (2.61); 0.8613 (1.65); 0.8494 (1.79); 0.8410 (1.16); 0.8295 (0.77); 0.8202 (0.45); 0.8154 (0.40); 0.8081 (0.67); 0.7881 (0.67); 0.7832 (0.64); 0.7772 (0.69); 0.7702 (0.59); 0.7658 (0.75); 0.7586 (0.33); 0.6934 (0.62); −0.0002 (6.53); −0.0084 (0.34)

| Example I-17, solvent: DMSO-d$_6$, spectrometer: 399.95 MHz |
| --- |

8.3192 (0.59); 7.9858 (16.00); 7.4606 (1.56); 7.4367 (4.09); 7.4123 (4.19); 7.3884 (1.63); 7.3160 (3.19); 7.1828 (7.31); 7.1702 (3.69); 7.0497 (3.58); 7.0341 (7.61); 6.9086 (10.84); 6.8986 (7.19); 6.1083 (2.81); 6.0869 (3.42); 6.0780 (3.39); 6.0564 (2.96); 5.9233 (0.75); 5.9097 (1.59); 5.8968 (1.64); 5.8831 (2.09); 5.8674 (2.27); 5.8536 (1.91); 5.8404 (1.99); 5.8272 (1.03); 5.7596 (12.92); 5.4694 (2.35); 5.4267 (6.85); 5.3797 (6.78); 5.3372 (6.61); 5.2915 (3.99); 5.1277 (4.64); 5.1013 (4.37); 4.6098 (0.83); 4.5972 (0.95); 4.5772 (4.62); 4.5648 (8.51); 4.5519 (4.63); 4.5334 (0.97); 4.5192 (0.86); 4.5083 (1.39); 4.3716 (2.33); 4.3401 (2.43); 4.0371 (0.32); 4.0197 (0.41); 3.9901 (2.15); 3.9563 (2.36); 3.8503 (2.27); 3.8194 (2.67); 3.8076 (3.44); 3.7769 (2.96); 3.5698 (3.79); 3.5492 (3.34); 3.5282 (2.56); 3.5067 (2.49); 3.4287 (1.43); 3.4197 (1.13); 3.4092 (1.81); 3.4000 (2.96); 3.3917 (1.89); 3.3809 (1.26); 3.3719 (1.72); 3.3322 (80.29); 3.3046 (2.09); 3.2739 (3.01); 3.2448 (1.60); 2.8900 (0.73); 2.8743 (1.52); 2.8441 (2.85); 2.8156 (1.54); 2.7311 (0.42); 2.6715 (2.00); 2.5525 (2.69); 2.5025 (299.09); 2.3292 (2.27); 2.1459 (2.12); 2.1112 (4.39); 2.0771 (2.51); 1.9895 (1.29); 1.8590 (0.74); 1.8508 (0.89); 1.8287 (1.83); 1.8219 (1.98); 1.7996 (1.83); 1.7923 (1.74); 1.7692 (0.75); 1.7606 (0.64); 1.6251 (0.72); 1.6155 (0.90); 1.5952 (1.81); 1.5861 (2.01); 1.5642 (1.86); 1.5557 (1.81); 1.5349 (0.77); 1.5251 (0.63); 1.3359 (1.62); 1.2981 (0.56); 1.2585 (0.77); 1.2494 (1.77); 1.2341 (0.61); 1.1930 (0.44); 1.1746 (0.70); 1.1571 (0.45); 1.1378 (6.70); −0.0002 (28.42)

-continued

Example I-18, solvent: DMSO-d$_6$, spectrometer: 399.95 MHz 7.9519 (12.77); 7.3153 (2.05); 7.2595 (5.62); 7.2546 (6.60); 7.2018 (5.65); 7.1970 (5.00); 7.1820 (4.90);
7.1688 (2.31); 7.0489 (2.36); 7.0328 (5.52); 6.9086 (4.64); 6.8970 (2.70); 6.2163 (1.88); 6.1931 (2.40);
6.1853 (2.22); 6.1620 (1.95); 5.7985 (0.50); 5.7847 (1.07); 5.7717 (1.08); 5.7580 (16.00); 5.7416 (1.38);
5.7284 (1.10); 5.7152 (1.25); 5.7017 (0.61); 5.4693 (1.24); 5.4267 (3.60); 5.3773 (3.53); 5.3349 (1.23);
5.2631 (2.60); 5.2593 (2.67); 5.2198 (2.20); 5.2160 (2.25); 5.0181 (2.44); 5.0149 (2.45); 4.9917 (2.22);
4.9885 (2.27); 4.6258 (0.77); 4.6123 (0.78); 4.5940 (2.10); 4.5807 (2.03); 4.5625 (2.07); 4.5483 (2.01);
4.5308 (0.78); 4.5165 (0.72); 4.3691 (1.10); 4.3368 (1.13); 4.0553 (0.40); 4.0375 (1.18); 4.0197 (1.22);
4.0017 (0.83); 3.9905 (1.01); 3.9562 (1.11); 3.7671 (1.49); 3.7359 (1.90); 3.7249 (2.54); 3.6939 (2.04);
3.5559 (2.19); 3.5327 (2.20); 3.5138 (1.59); 3.4907 (1.57); 3.4354 (0.40); 3.4259 (0.76); 3.4169 (0.57);
3.4066 (0.93); 3.3976 (1.58); 3.3884 (0.94); 3.3782 (0.62); 3.3690 (0.88); 3.3593 (0.59); 3.3279 (75.26);
3.3043 (2.20); 3.2757 (1.43); 3.2467 (0.75); 2.8765 (0.78); 2.8461 (1.36); 2.8185 (0.76); 2.6757 (0.34);
2.6709 (0.47); 2.6665 (0.34); 2.5410 (0.37); 2.5108 (26.24); 2.5064 (52.28); 2.5019 (69.42); 2.4974
(50.91); 2.4929 (24.96); 2.3332 (0.33); 2.3287 (0.47); 2.3240 (0.33); 2.1442 (0.95); 2.1092 (2.00);
2.0757 (1.10); 1.9890 (5.16); 1.8563 (0.34); 1.8468 (0.41); 1.8255 (0.88); 1.8173 (0.94); 1.7945 (0.87);
1.7859 (0.81); 1.7655 (0.34); 1.6238 (0.34); 1.6133 (0.42); 1.5924 (0.95); 1.5834 (0.96); 1.5624 (0.88);
1.5534 (0.85); 1.5322 (0.35); 1.3358 (0.63); 1.2585 (0.41); 1.2491 (0.82); 1.2352 (0.45); 1.1924 (1.41);
1.1746 (2.79); 1.1568 (1.36); 0.0844 (0.53); 0.0707 (0.38); 0.0079 (2.33); −0.0002 (57.94); −0.0085 (2.34)

Example I-19, solvent: DMSO-d$_6$, spectrometer: 399.95 MHz 8.3189 (0.39); 7.9626 (12.22); 7.3152 (1.99); 7.1819 (4.72); 7.1696 (2.36); 7.0488 (2.27); 7.0335 (5.32);
7.0053 (1.86); 6.9775 (1.90); 6.9603 (1.25); 6.9544 (1.02); 6.9370 (1.56); 6.9326 (2.02); 6.9275 (1.31);
6.9094 (5.97); 6.8978 (2.82); 6.0590 (1.58); 6.0363 (1.96); 6.0286 (1.87); 6.0056 (1.69); 5.7591 (16.00);
5.7252 (4.35); 5.7230 (4.39); 5.7212 (4.45); 5.4675 (1.26); 5.4403 (5.36); 5.4358 (5.54); 5.4251 (3.89);
5.3782 (3.64); 5.3357 (1.24); 4.7896 (11.21); 4.3666 (1.10); 4.3338 (1.17); 4.0373 (0.84); 4.0194 (0.86);
4.0014 (0.57); 3.9869 (1.02); 3.9524 (1.13); 3.8054 (1.09); 3.7750 (1.31); 3.7632 (1.69); 3.7325 (1.50);
3.5684 (1.81); 3.5457 (1.82); 3.5258 (1.32); 3.5032 (1.30); 3.4276 (0.37); 3.4183 (0.72); 3.4085 (0.54);
3.3991 (0.93); 3.3899 (1.54); 3.3806 (0.95); 3.3705 (0.68); 3.3613 (0.95); 3.3332 (104.96); 3.3063
(0.96); 3.3010 (1.00); 3.2709 (1.49); 3.2423 (0.82); 2.8725 (0.77); 2.8414 (1.40); 2.8145 (0.79); 2.6805
(0.32); 2.6760 (0.66); 2.6714 (0.92); 2.6668 (0.67); 2.5414 (0.34); 2.5247 (2.44); 2.5111 (52.04); 2.5069
(104.57); 2.5023 (139.02); 2.4978 (104.39); 2.4936 (53.31); 2.3337 (0.75); 2.3291 (1.01); 2.3245 (0.76);
2.1392 (0.95); 2.1053 (2.03); 2.0705 (1.18); 1.9894 (3.75); 1.8525 (0.36); 1.8439 (0.45); 1.8229 (0.89);
1.8145 (0.97); 1.7919 (0.92); 1.7839 (0.84); 1.7627 (0.38); 1.6201 (0.35); 1.6095 (0.44); 1.5888 (0.87);
1.5790 (0.97); 1.5581 (0.92); 1.5492 (0.88); 1.5287 (0.39); 1.3358 (0.67); 1.2493 (0.83); 1.1925 (1.01);
1.1747 (1.98); 1.1569 (0.97); 0.1459 (0.36); 0.0080 (2.93); −0.0002 (85.86); −0.0084 (3.77); −0.1497 (0.39)

Example I-20, solvent: DMSO-d$_6$, spectrometer: 399.95 MHz 8.0177 (0.50); 7.9663 (12.01); 7.3158 (2.02); 7.1825 (4.88); 7.1699 (2.48); 7.0494 (2.29); 7.0339 (5.47);
6.9095 (5.64); 6.8981 (3.92); 6.8859 (2.24); 6.8775 (2.09); 6.8739 (1.98); 6.8680 (1.34); 6.8508 (1.36);
6.8450 (1.00); 6.0534 (1.62); 6.0320 (1.93); 6.0228 (1.87); 6.0011 (1.71); 5.9005 (0.48); 5.8872 (1.02);
5.8740 (0.98); 5.8607 (1.23); 5.8441 (1.35); 5.8307 (1.20); 5.8175 (1.31); 5.8044 (0.64); 5.7593 (16.00);
5.4690 (1.24); 5.4264 (3.71); 5.3790 (3.71); 5.3378 (3.52); 5.3342 (3.48); 5.2948 (2.12); 5.2908 (2.18);
5.1247 (2.30); 5.1214 (2.37); 5.0983 (2.16); 5.0950 (2.23); 4.6331 (0.50); 4.6201 (0.49); 4.6007 (2.35);
4.5972 (1.88); 4.5882 (3.95); 4.5762 (2.34); 4.5570 (0.64); 4.5436 (0.56); 4.5087 (0.38); 4.3711 (1.11);
4.3379 (1.18); 4.0371 (0.66); 4.0194 (0.71); 4.0010 (0.64); 3.9893 (1.03); 3.9560 (1.13); 3.7900 (1.12);
3.7589 (1.33); 3.7471 (1.67); 3.7166 (1.45); 3.5152 (1.76); 3.4935 (1.80); 3.4726 (1.39); 3.4511 (1.36);
3.4338 (0.42); 3.4245 (0.72); 3.4153 (0.54); 3.4052 (0.91); 3.3960 (1.56); 3.3865 (0.98); 3.3770 (0.62);
3.3673 (0.87); 3.3576 (0.63); 3.3337 (91.42); 3.3088 (1.07); 3.3029 (1.05); 3.2718 (1.47); 3.2434 (0.84);
2.8724 (0.76); 2.8416 (1.38); 2.8148 (0.81); 2.6757 (0.62); 2.6712 (0.86); 2.6668 (0.64); 2.5525 (0.69);
2.5244 (2.32); 2.5110 (47.11); 2.5067 (94.65); 2.5022 (126.48); 2.4977 (95.53); 2.4934 (49.52); 2.3335
(0.70); 2.3290 (0.94); 2.3244 (0.71); 2.1427 (0.98); 2.1102 (2.06); 2.0752 (1.20); 1.9893 (2.96); 1.8579
(0.37); 1.8484 (0.48); 1.8267 (0.91); 1.8184 (0.98); 1.7966 (0.91); 1.7883 (0.85); 1.7671 (0.39); 1.6230
(0.38); 1.6129 (0.48); 1.5917 (0.91); 1.5829 (1.01); 1.5613 (0.94); 1.5518 (0.89); 1.5317 (0.41); 1.5211
(0.33); 1.3356 (1.57); 1.2979 (0.55); 1.2583 (0.82); 1.2491 (1.97); 1.2343 (0.97); 1.1924 (0.83); 1.1747
(1.56); 1.1569 (0.81); 1.1378 (2.06); 0.0079 (2.38); −0.0002 (69.49); −0.0084 (3.56)

Example I-21, solvent: DMSO-d$_6$, spectrometer: 399.95 MHz 7.9640 (12.03); 7.3189 (5.52); 7.3141 (8.26); 7.2767 (5.84); 7.2720 (4.94); 7.1815 (4.70); 7.1691 (2.24);
7.0483 (2.25); 7.0331 (5.18); 6.9085 (4.76); 6.8973 (2.56); 6.1891 (1.86); 6.1649 (2.40); 6.1584 (2.24);
6.1340 (1.93); 5.7579 (16.00); 5.4636 (1.17); 5.4210 (3.78); 5.3793 (3.69); 5.3367 (1.14); 4.8995 (0.50);
4.8936 (0.51); 4.8596 (4.21); 4.8522 (5.90); 4.8451 (4.17); 4.8111 (0.49); 4.8052 (0.49); 4.3699 (1.11);
4.3371 (1.18); 4.0553 (0.59); 4.0374 (1.80); 4.0196 (1.85); 4.0018 (1.04); 3.9894 (1.03); 3.9552 (1.12);
3.7725 (1.46); 3.7415 (1.85); 3.7302 (2.45); 3.6992 (1.98); 3.5621 (2.19); 3.5378 (2.21); 3.5198 (1.61);
3.4956 (1.59); 3.4756 (2.42); 3.4698 (5.27); 3.4640 (2.36); 3.4266 (0.40); 3.4188 (0.78); 3.4090 (0.56);
3.3995 (0.93); 3.3900 (1.60); 3.3810 (0.95); 3.3706 (0.65); 3.3611 (0.91); 3.3524 (0.83); 3.3282 (59.14);
3.3043 (2.05); 3.2708 (1.45); 3.2418 (0.78); 2.8735 (0.81); 2.8426 (1.40); 2.8151 (0.78); 2.6756 (0.35);
2.6709 (0.47); 2.6666 (0.36); 2.5064 (50.45); 2.5019 (67.00); 2.4974 (49.25); 2.4931 (24.03); 2.3286
(0.44); 2.3241 (0.34); 2.1495 (0.99); 2.1164 (1.96); 2.0804 (1.10); 1.9890 (7.82); 1.8487 (0.39); 1.8255
(0.88); 1.8194 (0.91); 1.7963 (0.82); 1.6264 (0.34); 1.6162 (0.40); 1.5952 (0.85); 1.5862 (0.92); 1.5645
(0.85); 1.5568 (0.81); 1.5356 (0.33); 1.3357 (0.61); 1.2585 (0.35); 1.2492 (0.75); 1.1924 (2.17); 1.1746
(4.27); 1.1568 (2.09); 0.0844 (0.48); 0.0707 (0.35); 0.0080 (2.15); −0.0002 (54.96); −0.0085 (1.95)

The intensity of sharp signals correlates with the height of the signals in a printed example of an NMR spectrum in cm and shows the true ratios of the signal intensities. In the case of broad signals, several peaks or the middle of the signal and their relative intensity may be shown in comparison to the most intense signal in the spectrum.

The lists of the 1H-NMR peaks are similar to the conventional 1H-NMR printouts and thus usually contain all peaks listed in a conventional NMR interpretation.

In addition, like conventional 1H-NMR printouts, they may show solvent signals, signals of stereoisomers of the target compounds, which are likewise provided by the invention, and/or peaks of impurities.

In the reporting of compound signals in the delta range of solvents and/or water, our lists of 1H-NMR peaks show the usual solvent peaks, for example peaks of DMSO in DMSO-$d_6$, and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks may therefore help to identify reproduction of our preparation process with reference to "byproduct fingerprints".

An expert calculating the peaks of the target compounds by known methods (MestreC, ACD simulation, or else with empirically evaluated expected values) can, if required, isolate the peaks of the target compounds, using additional intensity filters if appropriate. This isolation would be similar to the relevant peak picking in conventional 1H-NMR interpretation.

Use Examples

Example A

*Phytophthora* Test (Tomato)/Protective
Solvent: 49 parts by weight of N,N-dimethylformamide
Emulsifier: 1 part by weight of alkylaryl polyglycol ether An appropriate preparation of active ingredient is prepared by mixing 1 part by weight of active ingredient with the specified amounts of solvent and emulsifier, and diluting the concentrate with water to the desired concentration.

To test for protective activity, young tomato plants are sprayed with the preparation of active ingredient at the specified application rate. One day after the treatment, the plants are inoculated with a spore suspension of *Phytophthora infestans* and then stand for 24 hours at 100% relative humidity and 22° C. Thereafter the plants are placed in a climate cell at about 96% relative atmospheric humidity and at a temperature of about 20° C.

Evaluation takes place 7 days after inoculation. Here, 0% denotes an efficacy corresponding to that of the control, whereas an efficacy of 100% means that no infestation is observed.

In this test, the compounds of the invention below exhibit an efficacy of 70% or more at an active ingredient concentration of 100 ppm.

| Ex. No. | Eff. % |
|---|---|
| I-1 | 98 |
| I-2 | 94 |
| I-3 | 98 |
| I-4 | 95 |
| I-5 | 95 |
| I-18 | 95 |
| I-21 | 95 |

Example B

*Plasmopara* Test (Grapevine)/Protective
Solvent: 24.5 parts by weight of acetone
24.5 parts by weight of dimethylacetamide
Emulsifier: 1 part by weight of alkylaryl polyglycol ether An appropriate preparation of active ingredient is prepared by mixing 1 part by weight of active ingredient with the specified amounts of solvent and emulsifier, and diluting the concentrate with water to the desired concentration.

To test for protective activity, young plants are sprayed with the preparation of active ingredient at the specified application rate. After the spray coating has dried on, the plants are inoculated with an aqueous spore suspension of *Plasmopara viticola* and then spend 1 day in an incubation cabinet at about 20° C. and 100% relative atmospheric humidity. The plants are subsequently placed for 4 days in a greenhouse at about 21° C. and about 90% atmospheric humidity. The plants are then moistened and placed in an incubation cabin for 1 day.

Evaluation takes place 6 days after inoculation. Here, 0% denotes an efficacy which corresponds to that of the control, whereas an efficacy of 100% means that no infestation is observed.

In this test, the compounds of the invention below exhibit an efficacy of 70% or more at an active ingredient concentration of 10 ppm.

| Ex. No. | Eff. % |
|---|---|
| I-2 | 100 |
| I-3 | 100 |
| I-4 | 100 |
| I-5 | 96 |
| I-7 | 100 |
| I-8 | 100 |
| I-13 | 100 |
| I-17 | 100 |
| I-18 | 96 |
| I-19 | 100 |
| I-20 | 100 |
| I-21 | 100 |

The invention claimed is:
1. A compound of formula (I),

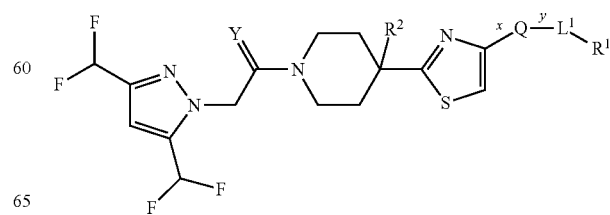

in which the definitions of radicals have the following meanings:
Y is oxygen,
$R^2$ is hydrogen,
Q is

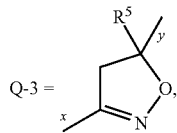

where the bond identified by "x" is bonded directly to the thiazole and the bond identified by "y" is bonded directly to $L^1$ or $R^1$,
$R^5$ is hydrogen or methyl,
$L^1$ is a direct bond,
$R^1$ is selected from the group consisting of 4,5-dimethyl-2-(prop-2-yn-1-yloxy)phenyl, 2,6-difluoro-3-(prop-2-yn-1-yloxy)phenyl, 2,6-difluoro-4-(prop-2-yn-1-yloxy)phenyl, 3-(allyloxy)-2,6-difluorophenyl, 2,6-difluoro-4-[(methylsulphonyl)amino]phenyl, 6-{[(2Z)-3-chloroprop-2-en-1-yl]oxy}-2,3-difluorophenyl, 6-[(2-chloroprop-2-en-1-yl)oxy]-2,3-difluorophenyl, 2,3-difluoro-6-(prop-2-yn-1-yloxy)phenyl, 4-[(cyclopropylcarbonyl)oxy]-2,6-difluorophenyl, 3,5-difluoro-2-(prop-2-yn-1-yloxy)phenyl, 4-(allyloxy)-2,6-difluorophenyl, 3,6-difluoro-2-(prop-2-yn-1-yloxy)phenyl, 2,4-difluoro-6-(prop-2-yn-1-yloxy)phenyl, 2,6-difluoro-4-formylphenyl, 2-(cyclopropylmethoxy)-4,6-difluorophenyl, 2-[(cylcopropylcarbonyl)oxy]-4,6-difluorophenyl, 6-(allyloxy)-2,3-difluorophenyl, 2-(allyloxy)-4,6-dichlorophenyl, 2-[(2-chloroprop-2-en-1-yl)oxy]-4,6-difluorophenyl, 2-(allyloxy)-4,6-difluorophenyl, and 2,4-dichloro-6-(prop-2-yn-1-yloxy)phenyl,
and/or a salt, metal complex and/or N-oxide of a compound of formula (I).

2. A compound of formula (I) and/or a salt, metal complex and/or N-oxide thereof according to claim 1, wherein $R^5$ is methyl.

3. A compound of formula (I) and/or a salt, metal complex and/or N-oxide thereof according to claim 1, wherein
Y is oxygen;
$R^2$ is hydrogen;
Q is Q-3;
$R^5$ is hydrogen;
$L^1$ is a direct bond;
$R^1$ is 4,5-dimethyl-2-(prop-2-yn-1-yloxy)phenyl or
$R^1$ is 2,6-difluoro-3-(prop-2-yn-1-yloxy)phenyl or
$R^1$ is 2,6-difluoro-4-(prop-2-yn-1-yloxy)phenyl or
$R^1$ is 2,6-difluoro-4-[(methylsulphonyl)amino]phenyl or
$R^1$ is 3-(allyloxy)-2,6-difluorophenyl or
$R^1$ is 4-(allyloxy)-2,6-difluorophenyl.

4. A method for controlling phytopathogenic harmful fungi, comprising delivering a compound of formula (I) and/or a salt, metal complex and/or N oxide thereof according to claim 1 to the phytopathogenic harmful fungi and/or a habitat thereof.

5. A composition for controlling phytopathogenic harmful fungi, comprising at least one compound of formula (I) and/or a salt, metal complex and/or N oxide thereof according to claim 1, and at least one extender and/or surfactant.

6. A compound and/or a salt, metal complex and/or N oxide of formula (I) according to claim 1 capable of being used for controlling phytopathogenic harmful fungi in agriculture, horticulture and forestry, in animal health, in materials protection and/or in a household and/or hygiene sector.

7. A method for producing a composition for controlling phytopathogenic harmful fungi, comprising mixing a compound of formula (I) and/or a salt, metal complex and/or N oxide according to claim 1 with at least one extender and/or surfactant.

8. The method according to claim 4 wherein the at least one compound and/or salt, metal complex and/or N oxide of formula (I) is applied to a transgenic plant.

9. The method according to claim 4 wherein the at least one compound and/or salt, metal complex and/or N oxide of formula (I) is applied to seed and/or seed of a transgenic plant.

10. A compound of formula (I) and/or a salt, metal complex and/or N-oxide thereof according to claim 1, wherein
$R^1$ is selected from the group consisting of 4,5-dimethyl-2-(prop-2-yn-1-yloxy)phenyl, 2,6-difluoro-3-(prop-2-yn-1-yloxy)phenyl, 2,6-difluoro-4-(prop-2-yn-1-yloxy)phenyl, 3-(allyloxy)-2,6-difluorophenyl, 2,6-difluoro-4-[(methylsulphonyl)amino]phenyl, 6-[(2-chloroprop-2-en-1-yl)oxy]-2,3-difluorophenyl, 2,3-difluoro-6-(prop-2-yn-1-yloxy)phenyl, 2,4-difluoro-6-(prop-2-yn-1-yloxy)phenyl, 6-(allyloxy)-2,3-difluorophenyl, 2-(allyloxy)-4,6-dichlorophenyl, 2-[(2-chloroprop-2-en-1-yl)oxy]-4,6-difluorophenyl, 2-(allyloxy)-4,6-difluorophenyl and 2,4-dichloro-6-(prop-2-yn-1-yloxy)phenyl.

11. The method according to claim 4 wherein the at least one compound and/or salt, metal complex and/or N oxide of formula (I) is applied to a fruit or vegetable.

12. The compound of formula (I) and/or a salt, metal complex and/or N-oxide thereof according to claim 1, wherein
Y is oxygen;
$R^2$ is hydrogen;
Q is Q-3;
$R^5$ is hydrogen;
$L^1$ is a direct bond; and
$R^1$ is 4-(allyloxy)-2,6-difluorophenyl.

13. A method for controlling phytopathogenic harmful fungi, comprising delivering a compound of formula (I) and/or a salt, metal complex and/or N oxide thereof according to claim 12 to the phytopathogenic harmful fungi and/or a habitat thereof.

14. A composition for controlling phytopathogenic harmful fungi, comprising at least one compound of formula (I) and/or a salt, metal complex and/or N oxide thereof according to claim 12, and at least one extender and/or surfactant.

* * * * *